(12) United States Patent
Liang et al.

(10) Patent No.: US 7,476,726 B1
(45) Date of Patent: Jan. 13, 2009

(54) METHOD OF PRODUCING AND PURIFYING ENDOSTATIN PROTEIN

(75) Inventors: Hong Liang, Gaithersburg, MD (US); Kim Lee Sim, Gaithersburg, MD (US); Amy Chang-Murad, DeRidder, LA (US); Xinhua Zhou, North Potomac, MD (US); John Madsen, Jefferson, MD (US); Renee J. Boerner, Apex, NC (US); Firoz Rustom Mistry, Chapel Hill, NC (US); Scot R. Shepard, Clayton, NC (US); Jeffrey L. Schrimsher, Hillsborough, NC (US); Lourdes L. Bermejo, Raleigh, NC (US)

(73) Assignees: The Children's Medical Center Corp., Boston, MA (US); Covance Biotechnology Services, Inc., Cary, NC (US)

( * ) Notice: Subject to any disclaimer, the term of this patent is extended or adjusted under 35 U.S.C. 154(b) by 79 days.

(21) Appl. No.: 10/070,560

(22) PCT Filed: Sep. 14, 2000

(86) PCT No.: PCT/US00/25166

§ 371 (c)(1), (2), (4) Date: Apr. 25, 2005

(87) PCT Pub. No.: WO01/19989

PCT Pub. Date: Mar. 22, 2001

Related U.S. Application Data

(60) Provisional application No. 60/153,698, filed on Sep. 14, 1999.

(51) Int. Cl.
*A23J 1/00* (2006.01)
*C07K 1/00* (2006.01)
*C12N 15/00* (2006.01)
*C12N 1/20* (2006.01)
*C12N 1/00* (2006.01)

(52) U.S. Cl. .................. 530/416; 530/412; 530/413; 530/414; 530/417; 530/350; 435/320.1; 435/252.3; 435/254.23

(58) Field of Classification Search .............. None
See application file for complete search history.

(56) References Cited

U.S. PATENT DOCUMENTS

| 4,666,865 | A | * | 5/1987 | Chang et al. ............ 436/518 |
| 5,854,205 | A |   | 12/1998 | O'Reilly et al. |
| 5,861,295 | A | * | 1/1999 | Goldstein et al. ......... 435/194 |
| 6,080,728 | A |   | 6/2000 | Mixson |

FOREIGN PATENT DOCUMENTS

| WO | WO 96/08274 A2 | 3/1996 |
| WO | WO 99/26480 A1 | 6/1999 |

OTHER PUBLICATIONS

O'Reilly et al 1997. Cell 88:277-285.*
Johansson et al. 1996. Journal of Biotechnology 48:9-14.*
Hjorth 1997. Tibtech 15:230-235.*
Trinh et al 2000. Bioseparation 9:223-230.*
Shiloach et al 2003. J. Chromatography B 790:327-336.*
Author: Boehm et al., Title: Disruption of the KEX1 Gene in *Pichia pastoris* Allows Expression of Full-Length Murine and Human Endostatin, Publ: *Yeast*, vol./Iss: 15, pp. 563-572, Date: 1999.
Author: Boehm et al., Title: Zinc-Binding of Endostatin is Essential for Its Antiangiogenic Activity, Publ: *Biochemical and Biophysical Research Communications*, vol./Iss: 252, pp. 190-194, Date: 1998.
Author: Dhanabal et al., Title: Endostatin: Yeast Production, Mutants, and Antitumor Effect in Renal Cell Carcinoma, Publ: *Cancer Research*, vol./Iss: 59, pp. 189-197, Date: Jan. 1, 199.
Author: John et al., Title: Novel Glycosylated Forms of Human Plasma Endostatin and Circulating Endostatin-Related Fragments of Collagen XV, Publ: *Biochemistry*, vol./Iss: 38 (32), pp. 10217-10224, Date: Aug. 10, 199.
Author: Shepard et al., Title: Purification of Recombinant Human Endostatin and Angiostatin from *Pichia pastoris* Fermentation Broth: Expanded Bed Adsoption Chromatography Method Development and Scale Up, Publ: *Abstracts of Papers American Chemical Society*, vol./Iss: 219 (1-2), pp. BIOT 212, Date: Mar. 26, 200.
Author: Standker et al., Title: Isolation and characterization of the circulating form of human endostatin, Publ: *FEBS Letters*, vol./Iss: 420, pp. 129-133, Date: 1997.

* cited by examiner

*Primary Examiner*—Elizabeth C. Kemmerer
*Assistant Examiner*—Shulamith H Shafer
(74) *Attorney, Agent, or Firm*—Kilpatrick Stockton, LLP

(57) ABSTRACT

The present invention provides a method for recombinant production, recovery and purification of endostatin protein. This method may be employed for large scale recovery and purification of recombinantly-produced endostatin protein.

13 Claims, 5 Drawing Sheets

Process Flow Diagram for Formulation/Fill/Finish
Formulation I: rhEndostatin/SOS

```
          ┌───────────┐ 1.1
          │ Thaw Bulk │
          └─────┬─────┘
                │       ┌──────────────────────────────┐ 1.2
                │◄──────│ Prepare PBS + 0.4 mM SOS buffer│
                ▼       └──────────────────────────────┘
 ┌──────────────────────────────────────────────┐ 1.3
 │ Diafilter (7x) to exchange to PBS + 0.4 mM SOS buffer │
 └───────────────────────┬──────────────────────┘
                         │      ┌──────────────────────────────────┐ 1.4
                         │◄─────│ Add 3.6 mM SOS to dialfiltered bulk │
                         ▼      └──────────────────────────────────┘
            ┌────────────────────────┐ 1.5
            │ Ultrafilter to 130 mg/mL │
            └───────────┬────────────┘
                        ▼
              ┌───────────────┐ 1.6
              │ Sterile Filter │
              └───────┬───────┘
                      ▼
        ┌────────────────────────────────┐ 1.7
        │ Fill into 3 cc vials at 1 mL per vial │
        └───────────────┬────────────────┘
                        ▼
               ┌────────────┐ 1.8
               │ Lyophilize │
               └──────┬─────┘
                      ▼
          ┌────────────────────────┐ 1.9
          │ Stopper and crimp seal │
          └────────────────────────┘
```

Note: The lyophilized product will be reconstituted with commercially available bottled Water For Injection (WFI)

Figure 1

SEQUENCE LISTING

```
<160> NUMBER OF SEQ ID NOS: 12

<210> SEQ ID NO 1
<211> LENGTH: 35
<212> TYPE: DNA
<213> ORGANISM: Artificial Sequence
<220> FEATURE:
<223> OTHER INFORMATION: Synthetic primer

<400> SEQUENCE: 1
tctctcgaga aaagacacag ccaccgcgac ttcca                              35

<210> SEQ ID NO 2
<211> LENGTH: 30
<212> TYPE: DNA
<213> ORGANISM: Artificial Sequence
<220> FEATURE:
<223> OTHER INFORMATION: Synthetic primer

<400> SEQUENCE: 2
atcgtctaga gcatccaggc ggtggctact                                    30

<210> SEQ ID NO 3
<211> LENGTH: 183
```

```
<212> TYPE: PRT
<213> ORGANISM: Homo sapiens

<400> SEQUENCE: 3

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Ser Glu Gly Pro Leu Lys Pro
                85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Lys
            180

<210> SEQ ID NO 4
<211> LENGTH: 549
<212> TYPE: DNA
<213> ORGANISM: Homo sapiens

<400> SEQUENCE: 4
cacagccacc gcgacttcca gccggtgctc cacctggttg cgctcaacag cccctgtca    60
ggcggcatgc ggggcatccg cggggccgac ttccagtgct tccagcaggc gcgggccgtg   120
gggctggcgg gcaccttccg cgccttcctg tcctcgcgcc tgcaggacct gtacagcatc   180
gtgcgccgtg ccgaccgcgc agccgtgccc atcgtcaacc tcaaggacga gctgctgttt   240
cccagctggg aggctctgtt ctcaggctct gagggtccgc tgaagcccgg gcacgcatc    300
ttctcctttg acggcaagga cgtcctgagg caccccacct ggccccagaa gagcgtgtgg   360
catggctcgg accccaacgg gcgcaggctg accgagagct actgtgagac gtggcggacg   420
gaggctccct cggccacggg ccaggcctcc tcgctgctgg ggggcaggct cctggggcag   480
agtgccgcga gctgccatca cgcctacatc gtgctctgca ttgagaacag cttcatgact   540
gcctccaag                                                           549

<210> SEQ ID NO 5
<211> LENGTH: 182
<212> TYPE: PRT
<213> ORGANISM: Homo sapiens

<400> SEQUENCE: 5

His Ser His Arg Asp Phe Gln Pro Val Leu His Leu Val Ala Leu Asn
1               5                   10                  15
```

```
Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Ser Glu Gly Pro Leu Lys Pro
                85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser
            180

<210> SEQ ID NO 6
<211> LENGTH: 181
<212> TYPE: PRT
<213> ORGANISM: Homo sapiens

<400> SEQUENCE: 6

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Ser Glu Gly Pro Leu Lys Pro
                85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala
            180
```

```
<210> SEQ ID NO 7
<211> LENGTH: 180
<212> TYPE: PRT
<213> ORGANISM: Homo sapiens

<400> SEQUENCE: 7

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Ser Glu Gly Pro Leu Lys Pro
                85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr
            180

<210> SEQ ID NO 8
<211> LENGTH: 179
<212> TYPE: PRT
<213> ORGANISM: Homo sapiens

<400> SEQUENCE: 8

Asp Phe Gln Pro Val Leu His Leu Val Ala Leu Asn Ser Pro Leu Ser
1               5                   10                  15

Gly Gly Met Arg Gly Ile Arg Gly Ala Asp Phe Gln Cys Phe Gln Gln
            20                  25                  30

Ala Arg Ala Val Gly Leu Ala Gly Thr Phe Arg Ala Phe Leu Ser Ser
        35                  40                  45

Arg Leu Gln Asp Leu Tyr Ser Ile Val Arg Arg Ala Asp Arg Ala Ala
    50                  55                  60

Val Pro Ile Val Asn Leu Lys Asp Glu Leu Leu Phe Pro Ser Trp Glu
65                  70                  75                  80

Ala Leu Phe Ser Gly Ser Glu Gly Pro Leu Lys Pro Gly Ala Arg Ile
                85                  90                  95

Phe Ser Phe Asp Gly Lys Asp Val Leu Arg His Pro Thr Trp Pro Gln
            100                 105                 110

Lys Ser Val Trp His Gly Ser Asp Pro Asn Gly Arg Arg Leu Thr Glu
        115                 120                 125

Ser Tyr Cys Glu Thr Trp Arg Thr Glu Ala Pro Ser Ala Thr Gly Gln
    130                 135                 140

Ala Ser Ser Leu Leu Gly Gly Arg Leu Leu Gly Gln Ser Ala Ala Ser
```

```
                145                 150                 155                 160
Cys His His Ala Tyr Ile Val Leu Cys Ile Glu Asn Ser Phe Met Thr
                    165                 170                 175

Ala Ser Lys

<210> SEQ ID NO 9
<211> LENGTH: 33
<212> TYPE: DNA
<213> ORGANISM: Artificial Sequence
<220> FEATURE:
<223> OTHER INFORMATION: Synthetic primer

<400> SEQUENCE: 9
tctctcgaga aaagagactt ccagccggtg ctc                                    33

<210> SEQ ID NO 10
<211> LENGTH: 537
<212> TYPE: DNA
<213> ORGANISM: Homo sapiens

<400> SEQUENCE: 10
gacttccagc cggtgctcca cctggttgcg ctcaacagcc ccctgtcagg cggcatgcgg        60
ggcatccgcg gggccgactt ccagtgcttc cagcaggcgc gggccgtggg gctggcgggc       120
accttccgcg ccttcctgtc ctcgcgcctg caggacctgt acagcatcgt gcgccgtgcc       180
gaccgcgcag ccgtgcccat cgtcaacctc aaggacgagc tgctgtttcc agctgggag        240 gctctgttct caggctctga gggtccgctg aagcccgggg cacgcatctt ctcctttgac       300
ggcaaggacg tcctgaggca ccccacctgg ccccagaaga gcgtgtggca tggctcggac       360
cccaacgggc gcaggctgac cgagagctac tgtgagacgt ggcggacgga ggctccctcg       420
gccacgggcc aggcctcctc gctgctgggg ggcaggctcc tggggcagag tgccgcgagc       480
tgccatcacg cctacatcgt gctctgcatt gagaacagct tcatgactgc ctccaag         537

<210> SEQ ID NO 11
<211> LENGTH: 178
<212> TYPE: PRT
<213> ORGANISM: Homo sapiens

<400> SEQUENCE: 11

Asp Phe Gln Pro Val Leu His Leu Val Ala Leu Asn Ser Pro Leu Ser
1               5                   10                  15

Gly Gly Met Arg Gly Ile Arg Gly Ala Asp Phe Gln Cys Phe Gln Gln
                20                  25                  30

Ala Arg Ala Val Gly Leu Ala Gly Thr Phe Arg Ala Phe Leu Ser Ser
            35                  40                  45

Arg Leu Gln Asp Leu Tyr Ser Ile Val Arg Arg Ala Asp Arg Ala Ala
        50                  55                  60

Val Pro Ile Val Asn Leu Lys Asp Glu Leu Leu Phe Pro Ser Trp Glu
65                  70                  75                  80

Ala Leu Phe Ser Gly Ser Glu Gly Pro Leu Lys Pro Gly Ala Arg Ile
                85                  90                  95

Phe Ser Phe Asp Gly Lys Asp Val Leu Arg His Pro Thr Trp Pro Gln
                100                 105                 110

Lys Ser Val Trp His Gly Ser Asp Pro Asn Gly Arg Arg Leu Thr Glu
            115                 120                 125

Ser Tyr Cys Glu Thr Trp Arg Thr Glu Ala Pro Ser Ala Thr Gly Gln
        130                 135                 140
```

```
Ala Ser Ser Leu Leu Gly Gly Arg Leu Leu Gly Gln Ser Ala Ala Ser
145                 150                 155                 160

Cys His His Ala Tyr Ile Val Leu Cys Ile Glu Asn Ser Phe Met Thr
                165                 170                 175

Ala Ser

<210> SEQ ID NO 12
<211> LENGTH: 26
<212> TYPE: PRT
<213> ORGANISM: Artificial Sequence
<220> FEATURE:
<223> OTHER INFORMATION: Synthetic peptide

<400> SEQUENCE: 12

Arg Ala Gly Pro Lys Leu Pro Gly Glu Ser Gly Ser Phe Leu Ala Glu
1               5                   10                  15

Trp Ser Pro Phe Leu Leu Glu Asp Lys Cys
            20                  25
```

METHOD OF PRODUCING AND PURIFYING ENDOSTATIN PROTEIN

RELATED APPLICATIONS

This application is a continuation of and claims benefit of priority from International Application No. PCT/US00/25166 (filed Sep. 14, 2000), which claims benefit of priority from U.S. Provisional Application No. 60/153,698 (filed Sep. 14, 1999).

FIELD OF THE PRESENT INVENTION

The present invention relates to a novel method of recombinantly producing, recovering and purifying endostatin protein (EntreMed. Inc., Rockville, Md.).

BACKGROUND OF THE INVENTION

Endostatin protein is a potent and specific inhibitor of endothelial proliferation and angiogenesis. Systemic or localized therapy with endostatin protein causes a nearly complete suppression of tumor-induced angiogenesis, and it exhibits strong anti-tumor activity. Endostatin protein has been isolated and purified from the murine hemangioendothelioma cell line EOMA, and is capable of inhibiting endothelial cell proliferation in cultured endothelial cells. Endostatin protein is a protein with a molecular weight of approximately 18,000 to 20,000 Daltons (18 to 20 kDa).

Endostatin protein is useful for treating diseases and processes mediated by undesired and uncontrolled angiogenesis by administering to a human or animal with the undesired angiogenesis a composition comprising a substantially purified endostatin protein or endostatin protein derivative, in a pharmaceutically acceptable carrier, in a dosage sufficient to inhibit angiogenesis. Endostatin protein is particularly useful for treating or for repressing the growth of tumors. Administration of endostatin protein to a human or animal with prevascularized metastasized tumors prevents the growth or expansion of those tumors.

Isolation and purification of proteins, such as endostatin protein, in high yield from biological material, such as tissue extracts, cell extracts, broth from incubation systems, and culture medium is often frought with problems in view of the numerous proteins and other undesirable molecules present in an homogenate or extract. What is needed are recombinant methods of producing endostatin protein that will provide the large amounts of endostatin protein required for clinical use, including, but not limited to, cancer therapy. Such methods should produce endostatin protein in an efficient and convenient manner in a culture broth which is amenable to procedures designed to recover and purify endostatin protein in high yields. Separating a specific protein of interest from potential contaminants presents a challenge in view of numerous factors, such as contamination of cellular homogenates with proteolytic enzymes that may digest the protein. Other undesirable cellular constituents that may be present in homogenates, include but not limited to, pigments, cytochromes, lipids, free radicals, oxidases and other lysosomal enzymes, and oxides. Some of these substances may affect the protein of interest by stripping electrons, affecting disulfide bonds and changing the conformation of the protein.

Centrifugation of cells, including yeast, bacteria, insect and other cells used for recombinant production of proteins, such as endostatin protein, may result in damage to the cells with concomitant release of undesirable biological material. What is needed is a method for recovery and purification of protein, such as endostatin protein, which does not employ centrifugation.

Methods for recombinant production, recovery and purification of endostatin protein on a large scale are required to produce and isolate the amounts of purified endostatin protein needed for administration to patients and also for research purposes.

Solutions are also needed for storage of endostatin protein after recovery and purification, which provide desired solubility and stability of endostatin protein. Since large quantities of purified endostatin protein are needed for use in the clinic and in research laboratories, it is necessary to determine the proper conditions for solubility of the endostatin protein so that it may be stored conveniently at different temperatures while preserving biological activity. Optimal buffer systems are also needed for lyophilization of endostatin protein. Lyophilization of endostatin protein would permit periods of extended storage before conveniently reconstituting endostatin protein in an appropriate buffer system, as needed, before use. It is advantageous to reconstitute lyophilized proteins prior to clinical administration to humans or animals. Accordingly, what is needed are optimal solubility conditions for the endostatin protein, especially recombinantly produced endostatin protein. What is also needed are methods for recovering and/or purifying endostatin protein, particularly recombinantly-produced endostatin protein. Such conditions involving the optimal solutions and solubility conditions to facilitate storage, lyophilization and reconstitution, must not have deleterious effects on the biological activity of endostatin protein.

Also needed is a method for purifying recombinantly-produced endostatine protein which avoids the need for centrifugation of the culture broth, thereby avoiding problems associated with cell lysis. This method should be capable of use on a large scale to recover and purify endostatin protein in quantities needed for clinical administration and research.

What is also needed is a method for purifying recombinantly-produced endostatinprotein which minimizes contamination with cytochromes, pigments, enzymes, and other undesirable cellular constituents.

Also needed are solutions for storage of endostatin protein following the recovery and purification process which optimizes solubility properties of endostatin protein.

SUMMARY OF THE INVENTION

The present invention solves these problems inherent in the recovery and purification of proteins, particularly endostatin protein, by providing new and useful methods for recombinant production, recovery and purification of proteins, especially endostatin protein. The present invention provides new and useful methods for recombinantly producing endostatin protein in large amounts. The present invention provides a method for recovery and purification of endostatin protein. The present invention also provides new and useful solutions for storage of endostatin protein and also for lyophilization of endostatine protein. These methods provide the benefit of preserving the biological activity of endostatin protein. Preservation of the biological activity of endostatin protein is crucial for administration of endostatin protein to humans and animals for the purpose of inhibition of undesirable angiogenesis, for other biological activities, and for research investigations or other types of biological testing.

Endostatin protein is effective in treating diseases or processes that are mediated by, or involve, angiogenesis. The angiogenesis mediated diseases include, but are not limited to, solid tumors; blood born tumors such as solid tumors, blood borne tumors, leukemias; tumor metastases; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, colon cancer, retrolental fibroplasia, rubeosis; Osler-Webber Syndrome; myocardial angiogenesis; plaque neovascularization; telangiectasia; hemophiliac joints; angiofibroma; and wound granulation. Endostatin protein is useful in the treatment of disease of excessive or abnormal stimulation of endothelial cells. These diseases include, but are not limited to, intestinal adhesions, atherosclerosis, scleroderma, and hypertrophic scars, i.e., keloids. Endostatin protein can be used as a birth control agent by preventing vascularization required for blastocyst implantation and for development of the placenta, the blastocyst, the embryo and the fetus. The methods of the present invention provide means to produce, isolate and purify Endostatin protein in the large amounts needed for the numerous applications described in this paragraph.

Endostatin protein specifically and reversibly inhibits endothelial cell proliferation. Endostatin protein is useful as a birth control drug, and for treating angiogenesis-related diseases, particularly angiogenesis-dependent cancers and tumors. Endostatin protein is also useful for curing angiogenesis-dependent cancers and tumors. The ability of endostatin protein to treat and cure angiogenesis-dependent cancers and tumors answers a long-felt and unfulfilled need in the medical arts, and provides an important benefit to mankind.

In one embodiment, the present invention provides new and improved methods for recombinant production of biologically active endostatin protein in high yield.

In another embodiment, the method of the present invention is useful for recovery and purification of recombinantly-produced endostatin protein.

In another embodiment, the method of the present invention is useful for recovery and purification of endostatin protein from extracts of biological fluids, cells and tissues.

An advantage of the present invention is that higher amounts of biologically active endostatin protein are recombinantly produced. Another advantage of the present invention is that greater amounts of endostatin protein are recovered than obtained with prior art methods. Yet another advantage of the present invention is that higher yields of more purified, and biologically active endostatin protein are obtained. Still another advantage of the present invention is that endostatin protein may be stored in buffers for extended periods of time, and also subjected to lyophilization, while preserving biological activity. An advantage of the present invention is that it permits Endostatin™ protein to be stored in vials or other containers, either in a solution which may be liquid or frozen, or lyophilized, and optionally shipped to a recipient.

Accordingly, an object of the present invention is to provide an improved method for recombinant production of large amounts of biologically active endostatin protein.

Another object of the present invention is to provide a method for recovery and purification of recombinantly produced proteins.

Yet another object of the present invention is to provide a method for recovery and purification of endostatin protein.

Another object of the present invention is to provide a method for recovery and purification of endostatin protein, particularly recombinantly produced endostatin protein.

An advantage of the purification methods of the present invention is that undesirable proteins, lipids and pigments are efficiently separated from the desired protein, especially endostatin protein.

It is another object of the present invention to provide solutions which provide favorable solubility conditions for endostatin protein, particularly recombinantly-produced endostatin protein while retaining biological activity of endostatin protein.

Yet another object of the present invention is to provide solutions which provide favorable solubility conditions for lyophilization of endostatin protein, particularly recombinantly-produced endostatin protein.

Another advantage of the methods of the present invention is that centrifugation of the broth from fermentation steps in recombinant production of endostatin protein is avoided, thereby preventing unwanted potential cellular lysis and potential contamination of endostatin protein with additional proteins, pigments, enzymes and other cellular chemicals and debris.

Another object of the present invention is to provide methods amenable to large scale production, recovery and purification of recombinantly-produced endostatin protein.

Another advantage of the present invention is that the recovered and purified endostatin protein is provided in a solution which optimizes solubility of endostatin protein, while preserving the bioactivity of endostatin protein.

These and other objects, features and advantages of the present invention will become apparent after a review of the following detailed description.

BRIEF DESCRIPTION OF THE DRAWINGS

FIG. 1 is a process flow diagram for the large scale purification described in Example 8.

DETAILED DESCRIPTION

Figure 2:
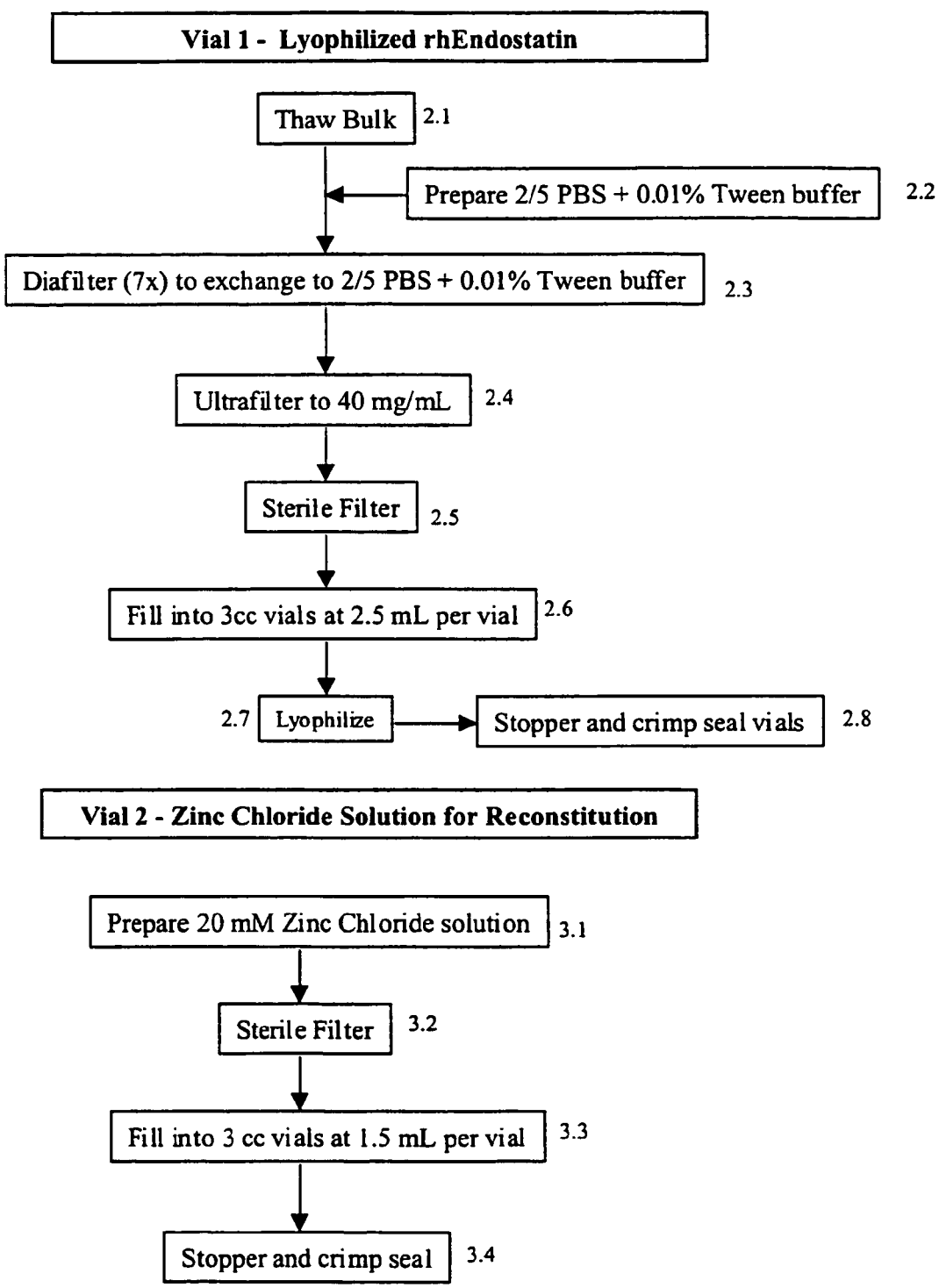
FIG. 2 is a process flow diagram for the large scale purification described in Example 9.
Figure 3A:
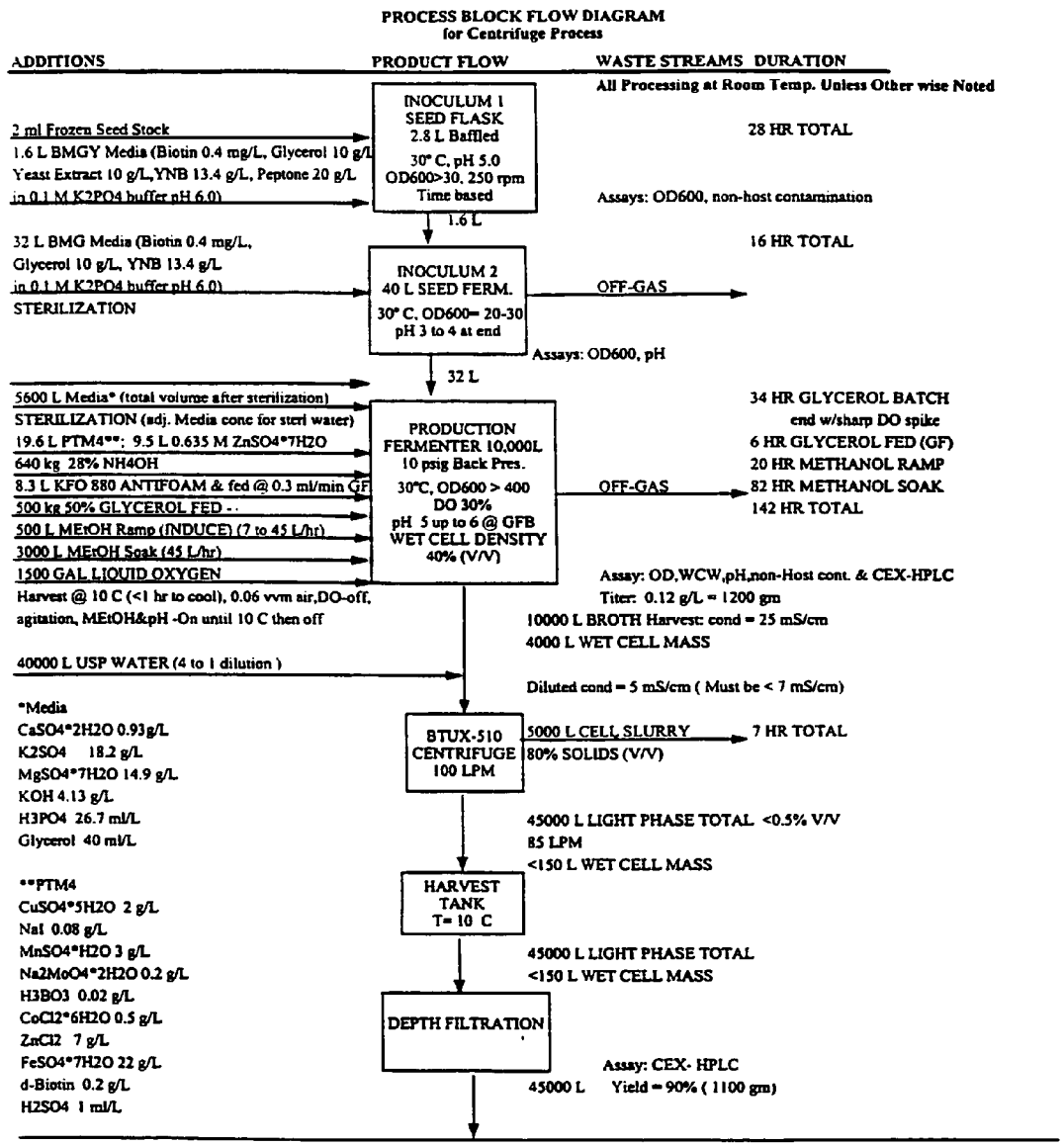
FIG. 3 is a schematic representation of a process for a large scale production and purification of endostatin protein.
Figure 3B:
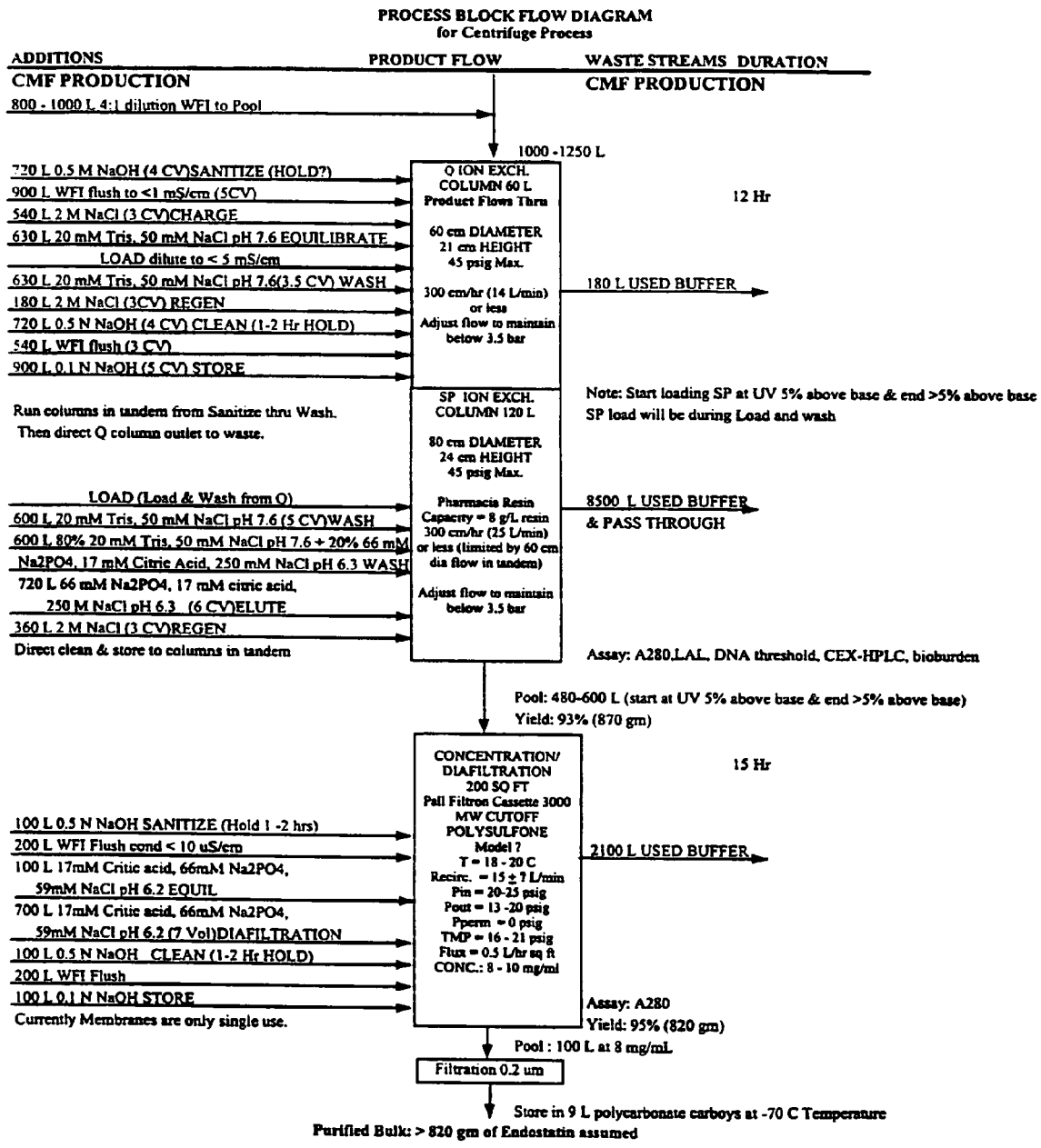
Figure 3C:
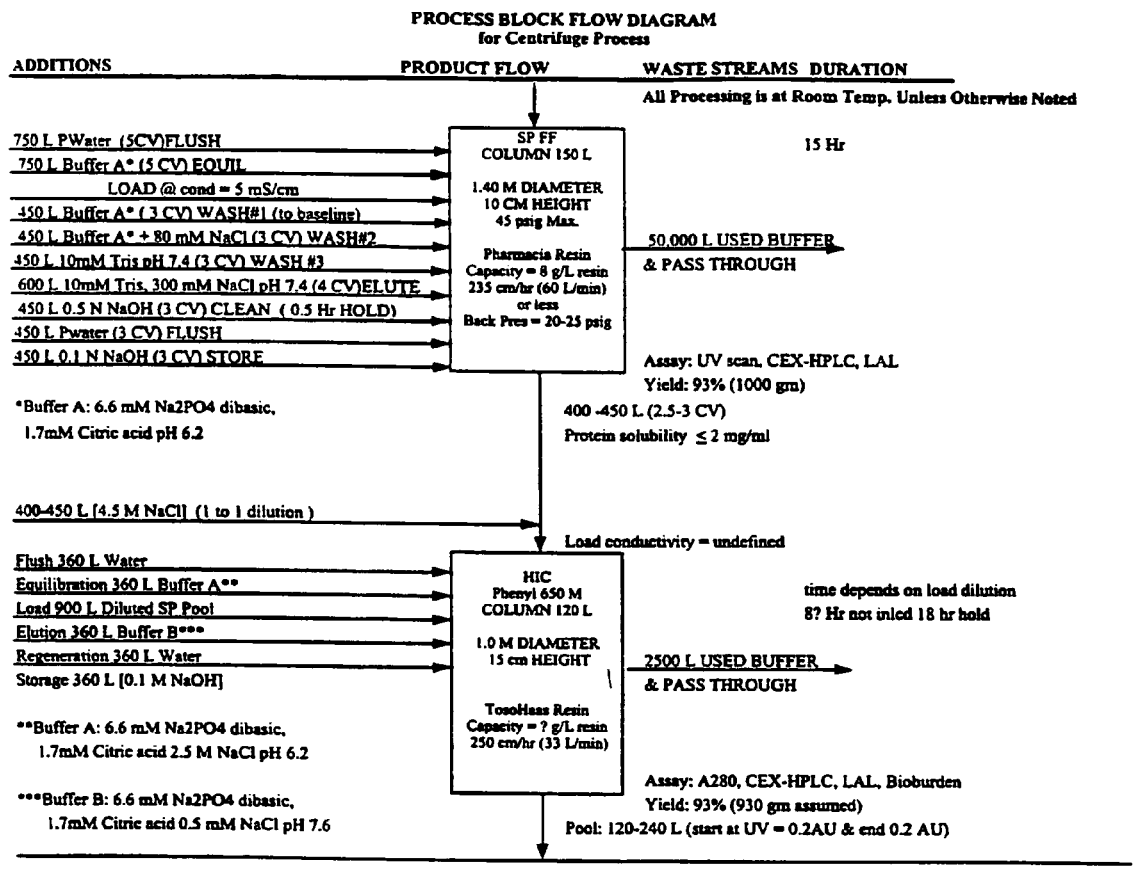

The method can serve as a large scale purification protocol for obtaining an endostatin protein formulation which may be used in clinical human trials. In one aspect, the protocol involves thawing the bulk, diafiltration with PBS and SOS, ultrafiltration, and lyophilization. In another aspect, the protocol involves thawing the bulk, diafiltration with PBS and Tween, ultrafiltration, lyophilization and addition of zinc chloride.

DEFINITIONS

Definitions for other terms used herein are as follows. The terms "a", "an" and "the" as used herein are defined to mean "one or more" and include the plural unless the context is inappropriate. As used herein, the terms "detecting" or "detection" refer to qualitatively or quantitatively determining the presence of a molecule under investigation.

"Proteins", "peptides", "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the peptide, or to the alpha-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids making up a peptide are numbered in order, starting at the amino terminal and increasing in the direction toward the carboxy terminal of the peptide. Thus, when one amino acid is said to "follow" another, that amino acid is positioned closer to the carboxy terminal of the peptide than the preceding amino acid.

The term "residue" is used herein to refer to an amino acid (D or L) or an amino acid mimetic that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The term "endostatin protein" refers to a protein that is preferably 18 kDa to 20 kDa in size as determined by non-reducing and reducing gel electrophoresis, respectively. The term "endostatin protein" refers to proteins that may be synthesized and may be isolated from biological tissues, cells, cell culture medium, and from broth and media obtained from cellular and cell-free expression systems. Accordingly, the term endostatin protein includes endostatin protein produced from recombinant expression systems. The term endostatin protein also includes precursor forms of the 18 kDa to 20 kDa protein endostatin protein. The term endostatin protein also includes fragments of the 18 kDa to 20 kDa protein, and modified proteins and peptides thereof that have a substantially similar amino acid sequence, and that are capable of inhibiting proliferation of endothelial cells. For example, silent substitutions of amino acids, wherein the replacement of an amino acid with a structurally or chemically similar amino acid does not significantly alter the structure, conformation or activity of the protein, are well known in the art. Such silent substitutions are intended to fall within the scope of the present invention. The term endostatin protein also includes various post-translational modifications or other modifications of endostatin protein, including, but not limited to, phosphorylation, glycosylation, sulfation, and disulfide bond formation or reduction.

It will be appreciated that the term "endostatin protein", as used herein, includes shortened proteins or peptide fragments of endostatin protein wherein one or more amino acids, preferably 1 to 10 amino acids, are removed from either or both ends of endostatin protein, or from an internal region of the protein, yet the resulting molecule retains bioactivity such as endothelial proliferation inhibiting activity. The term "endostatin protein" also includes lengthened proteins or peptides wherein one or more amino acids, preferably 1 to 10 amino acids, is added to either or both ends of endostatin protein, or to an internal location in the endostatin protein, yet the resulting molecule retains endothelial proliferation inhibiting activity.

Also included in the definition of the term endostatin protein are modifications of the endostatin protein, its subunits and peptide fragments. Such modifications include substitutions of naturally occurring amino acids at specific sites with other molecules, including but not limited to naturally and non-naturally occurring amino acids. Such substitutions may modify the bioactivity of endostatin protein and produce biological or pharmacological agonists or antagonists. Such substitutions may include conservative substitutions known to one of skill in the art, such as valine for alanine. Acceptable substitutions may also include modifications of amino acids, such as norleucine for leucine. It is to be understood that substitution of D amino acids for L amino acids is encompassed within the scope of the present invention. Some substitutions are described in *Dictionary of Biochemistry and Molecular Biology,* 2nd ed., J. Stenesh, John Wiley & Sons, 1989, the entirety of which is incorporated herein by reference. Additional modifications include addition of an amino acid, such as a tyrosine or another amino acid at specific locations in endostatin protein or fragments thereof to enhance labeling potential with radioactive and non-radioactive labels, addition of molecules such as ricin, addition of radioactive and/or non-radioactive labels.

"Substantial sequence homology" means at least approximately 70% homology between the acid residue sequence in the endostatin protein analog sequence and that of endostatin protein, preferably at least approximately 80% homology, more preferably at least approximately 90% homology.

Furthermore, one of skill in the art will recognize that individual substitutions, deletions or additions in the amino acid sequence of endostatin protein, or in the nucleotide sequence encoding for the amino acids in the endostatin protein, which alter, add or delete a single amino acid or a small percentage of amino acids (typically less than 5%, more typically less than 1%) in an encoded sequence are conservatively modified variations, wherein the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Methods of Producing Endostatin Protein

Endostatin protein can be isolated from biological sources, including tissues, cells and biological fluids. Endostatin protein has been isolated from murine hemangioendothelioma (EOMA). Endostatin protein may be produced from recombinant sources, from genetically altered cells implanted into animals, from tumors, and from cell cultures, as well as other sources. Endostatin protein can be isolated from body fluids including, but not limited to, serum, urine and ascites, or synthesized by chemical or biological methods (e.g. cell culture, recombinant gene expression, cellular and cell free expression systems, peptide synthesis, and in vitro and in vivo enzymatic catalysis of precursor molecules to yield active endostatin protein). Recombinant techniques include gene amplification from DNA sources using the polymerase chain reaction (PCR), and gene amplification from RNA sources using reverse transcriptase/PCR.

Endostatin protein can be made by automated protein synthesis methodologies well known to one skilled in the art. Alternatively, endostatin protein may be isolated from larger known proteins, such as human alpha 1 type XVIII collagen and mouse alpha 1 type XVIII collagen, proteins that share a common or similar N-terminal amino acid sequence. Examples of other potential endostatin protein source materials having similar N-terminal amino acid sequences include *Bos taurus* pregastric esterase, human alpha 1 type 15 collagen, NAD-dependent formate dehydrogenase (EC 1.2.1.2) derived from *Pseudomonas* sp., s11459 hexon protein of bovine adenovirus type 3, CELF21D12 2 F21d12.3 *Caenorhabditis elegans* gene product, VAL1 TGMV AL1 protein derived from tomato golden mosaic virus, s01730 hexon protein derived from human adenovirus 12, *Saccharomyces cerevisiae*. For example, peptides closely related to endostatin protein may be derived from BOVMPE 1 pregastric esterase (BOS TAURUS) gene sequence corresponding to amino acids 502 to 521, and collagen alpha 1 type 15 from humans beginning at amino acid 316 ending at 335. Endostatin protein can also be produced synthetically by chemical reaction or by recombinant techniques in conjunction with expression systems.

It is contemplated as part of the present invention that endostatin protein can be isolated from a body fluid such as blood or urine of patients. Endostatin protein can also be produced by recombinant DNA methods or synthetic peptide chemical methods that are well known to those of ordinary skill in the art. In a preferred embodiment of the present invention, endostatin protein is recombinantly produced. A preferred method of recombinant production of endostatin protein is a method employing *Pichia pastoris*. Novel methods of isolation and purification of endostatin protein, especially recombinantly-produced endostatin protein are provided in the present invention. Method for assaying for the biological activity of endostatin protein, and assaying for inhibitor activity is provided in U.S. Pat. No. 5,854,205 which is incorporated herein by reference in its entirety.

It is to be understood that a variety of expression systems may be used for recombinant production of endostatin protein. These expression systems include, but are not limited to *Pichia pastoris*, yeast, *E. coli*, insect cells, baculovirus expressions systems, expression in transgenic animals, expression in transgenic plants, mammalian systems, and other systems commonly known to one of ordinary skill in the art of expressing proteins. Some of these expression systems are described in U.S. Pat. No. 5,854,205. Although the *Pichia pastoris* expression system was used for most of the recombinant endostatin protein production presented in the present application, it is to be understood that the present invention encompasses other systems for recombinant production of endostatin protein. Accordingly, modifications of the endostatin protein production parameters presented herein can be made by one of ordinary skill in the art of recombinant production of proteins using specific expression systems. For example, when yeast are used for recombinant production of endostatin protein, different induction methods may be used, as commonly known to one of skill in the art. Yeast can be induced on methanol, or a mixture of methanol and glycerol, all optionally diluted with water, at feed rates commonly known to one of ordinary skill in the use of yeast expression systems for recombinant production of molecules, including proteins.

Culture Conditions

The following description of a preferred embodiment of the culture conditions for endostatin protein is not limiting to the invention, and it is to be understood that the conditions, described here and in the examples may be scaled up or down to accommodate higher or lower requirements for production of endostatin protein. These conditions may be scaled up to accommodate endostatin protein production by 5, 10, 20 or 100 fold. It is also to be understood that the various concentrations of solutions and reagents described herein, including description contained in the Tables are not limiting and may be increased or decreased in a range of 0 to 20%, preferably 0 to 10%, without altering the spirit and scope of the present invention.

Seed Culture

Inoculum cultures are prepared using a two stage seed process of *Pichia pastoris*. The first stage employs an enriched media (about 800 mL in a 2.8 L flask) and is incubated at 250 rpm and about 30° C. for approximately 24 hours to a final optical density at 600 nm ($OD_{600\ nm}$) of greater than 30. The second stage uses a similar media base (16×1 L in 2.8 L shaker flasks) and is incubated at about 250 rpm and 30° C. for approximately 16 hours to a final $OD_{600\ nm}$, of between about 20.0 and 30.0.

Main Fermentation

The fermentation media consists of calcium sulfate, potassium sulfate, magnesium sulfate, potassium hydroxide, phosphoric acid and glycerol. Post sterilization addition of trace salts solution is also necessary. The fermentation process consists of four main phases; batch glycerol, fed-batch glycerol, methanol ramp and methanol soak.

The batch glycerol phase is the beginning phase which utilizes the initial charge of glycerol as the carbon source. This phase lasts for approximately 28 hours. The end of this phase is characterized by a sharp dissolved oxygen (DO) spike. The spike indicates the depletion of the carbon source.

The fed-batch glycerol phase is initiated at a set flow (about 16.6 g/kg/hr) immediately following the batch glycerol phase. The fed-batch glycerol phase lasts for about 6 hours. During the final two hours of the fed-batch phase, the pH is ramped linearly from 5.0 to 6.0.

The methanol ramp phase is initiated immediately following the fed-batch glycerol phase. The methanol is used as a carbon source and as a product inducer. In this system, endostatin protein is produced as a secreted protein. During this phase, the methanol flow rate to the fermentor is ramped linearly from about 1.3 to 8.0 mL/kg/hr over a period of approximately 4.8 hour.

The final phase of the fermentation is the methanol induction phase. The methanol is used as a carbon source and product inducer. During this phase the methanol is fed to the fermentor at a set rate between about 4.0 and 12.0 mL/kg/hr, with a preferred rate of about 8.0 mL/kg/hr for a sufficient amount of time between about 60 and 100 hours. In a preferred embodiment, the methanol feed rate is about 8.0 mL/kg/hr for about 81.2 hours.

Next, harvest conditions are set, and after the conditions are achieved, the medium is ready for harvest. To minimize foaming, the methanol and pH loops are not shutoff until the temperature is below 20° C. The final endostatin protein concentration was approximately 120 mg/L in the supernatant. The final wet cell weight (WCW) is approximately 400 g/L.

Many of the solutions and other conditions used in the incubation are shown in the following tables. It is to be understood that these conditions are not limiting, and that they may be increased or decreased to accommodate scale up or scale down of the procedure to attain a desired production level of endostatin protein.

Fermentation

TABLE 1

| Seed Culture 1st Stage | | |
|---|---|---|
| Media Components/Concentration: | Biotin | 0.4 mg/L |
| | Glycerol | 10 g/L |
| | Yeast Nitrogen Base | 13.4 g/L |
| | Peptone | 20 g/L |
| | Yeast Extract | 10 g/L |
| | Potassium Phosphate Buffer, pH 6.0 | 0.1 M |
| Shake Volume: | 800 mL | |
| Inoculum Size: | 1.0 mL | |
| Incubation Conditions: | 250 rpm And 30° C. | |
| Incubation end Conditions: | OD 600 nm >30 (approximately 24 hours) | |

TABLE 2

| 2nd Stage | | |
|---|---|---|
| Media Components/Concentration: | Biotin | 0.4 mg/L |
| | Glycerol | 10 g/L |
| | Yeast Nitrogen Base | 13.4 g/L |
| | Potassium Phosphate Buffer, pH 6.0 | 0.1 M |
| Shake Volume: | 16 × 1 L | |
| Inoculum Size: | Such that initial OD 600 nm = 0.85 ± 0.15 | |
| Incubation Conditions: | 250 rpm and 30° C. | |
| Incubation end Conditions: | OD 600 nm 30—30 (approximately 16 hours) | |
| Testing | Non-host Contamination | |

Fermentation

TABLE 3

| Fermentation Preinoculum Specifications | | |
|---|---|---|
| Media Components/Concentration: | Calcium sulfate, dihydrate ($CaSO_4 \cdot 2H_2O$) | 0.93 g/L |
| | Potassium sulfate ($K_2SO_4$) | 18.2 g/L |
| | Magnesium sulfate ($MgSO_4 \cdot 7H_2O$) | 14.9 g/L |
| | Potassium hydroxide (KOH) | 4.13 g/L |
| | Phosphoric acid ($H_3PO_4$) | 26.7 mL/L |
| | Glycerol | 40 mL/L |
| Density: | 1.05 kg/L | |
| Pre SIP Volume: | 815 L (856 kg) | |
| Post SIP Volume: | 839 L (881 kg) | |
| Sterile Additions: | $PTM_4$ Trace salts (see Table 4) | 3.5 mL/L |
| | 0.635 M Zinc sulfate solution (see Table 5) | 1.7 mL/L |
| Antifoam: | KFO 880 ~0.25 to 1.5 L as required | |
| Testing | Media hold (sterility) | |

TABLE 4

| $PTM_4$ Solution | | |
|---|---|---|
| Component and Concentration: | Cupric sulfate ($CuSO_4 \cdot 5H_2O$) | 2 g/L |
| | Sodium iodide (NaI) | 0.08 g/L |
| | Manganese sulfate ($MnSO_4 \cdot H_2O$) | 3 g/L |
| | Sodium molybdate ($Na_2MoO_4 \cdot 2H_2O$) | 0.2 g/L |
| | Boric acid ($H_3BO_3$) | 0.02 g/L |
| | Cobalt chloride ($CoCl_2 \cdot 6H_2O$) | 0.5 g/L |
| | Zinc chloride ($ZnCl_2$) | 7 g/L |
| | Ferric Sulfate ($FeSO_4 \cdot 7H2O$) | 22 g/L |
| | d-Biotin | 0.2 g/L |
| | Sulfuric acid ($H_2SO_4$) | 1 mL/L |

TABLE 5

| 0.635 M Zinc Sulfate Solution | | |
|---|---|---|
| Component and Concentration: | Zinc sulfate | 183 g/L |

TABLE 6

| Batch Glycerol Phase and Fermentation Conditions | |
|---|---|
| Carbon Source: | Initial charge of glycerol |
| Temperature: | 30° C. |
| pH: | 5.0 |
| Agitation: | 250 rpm |
| Aeration: | 0.666 vvm (per initial weight) |
| DO: | 30% (controlled by oxygen supplementation) |
| Back-pressure: | 3 psig |
| In Process Testing: | Wet cell weight, OD 600 nm, offline pH, and methanol concentration |
| Duration: | ~26 hours |

TABLE 7

| Fed-Batch Glycerol Phase | |
|---|---|
| Purpose: | Expansion of cell density |
| Start: | Approximately fermentation hour 28 |
| Flowrate: | 16.6 g/kg/hr (per kg of initial weight) |
| Duration: | 6 hours |
| Glycerol Specifics | 50% glycerol solution (by weight) with KFO 880 antifoam (0.2 mL/kg) |
| pH Shift Start: | 4th hour of fed batch glycerol |
| pH Shift Specifics: | Linear decrease from 5.0 to 6.0 |
| pH Shift Duration: | 2 hours |

TABLE 8

| Methanol Adaptation Phase | |
|---|---|
| Purpose: | Methanol as inducer and carbon source |
| Start: | Immediately following Fed-Batch Glycerol Phase |
| Initial Flowrate: | 1.3 mL/kg/hr (per kg of initial weight) |
| Final Flowrate: | 8.0 mL/kg/hr (per kg of initial weight) |
| Ramp Rate: | 1.4 mL/kg/hr$^2$ |
| Duration: | 4.8 hours |

TABLE 9

Methanol
Induction Phase

| | |
|---|---|
| Start: | Immediately following Methanol Ramp Phase |
| Flowrate: | 8.0 mL/kg/hr (per kg of initial weight) |
| Duration: | 81.2 hours |
| Specifics: | Oxygen consumption ~0.188 slpm/kg (per kg of initial weight) |

TABLE 10

Harvest
Conditions

| | |
|---|---|
| Temperature: | 10° C. |
| Agitation: | 50 rpm |
| Aeration: | 50 slpm |
| DO: | OFF |
| Back-pressure: | 3 psig |
| Specifics: | Methanol and pH loops on until <20° C. is met<br>Endostatin protein Concentration ~0.12 mg/L in supernatant<br>Final Weight of ~1450 kg<br>Final WCW of ~400 g/L |
| QC Testing: | Non-Host Contamination and CEX HPLC |

Method for Isolation and Purification of Endostatin Protein

The present invention also provides a new and useful method for recovery and purification of proteins, particularly recombinantly-produced proteins. The methods of the present invention may be used for recovery and purification of endostatin protein from biological sources, including but not limited to biological fluids, tissues, cells, culture media, and fermentation media. In one embodiment, the present invention provides a new and useful method for recovery and purification of endostatin protein, and more particularly, recombinantly-produced endostatin protein. This method may be employed for large scale recovery and purification of recombinantly-produced endostatin protein. It is to be understood that the present invention is useful for recovery and purification of endostatin protein from any expression system.

The basic recovery process of endostatin protein is accomplished using four chromatography steps and a final concentration and diafiltration step. The final formulated material exists as a clear to slightly-pink solution at a concentration of about 8 mg/ml. It may be stored and shipped as a frozen liquid (for example, at a temperature of −70° C. to −90° C.) or lyophilized.

Upon completion of fermentation, the broth, which consists of all components (cells, nutrients, and buffer) within the fermenter, is diluted with water to a conductivity that favors binding of the target protein to the first column in the process.

The first chromatography step in the recovery and purification procedure is called the endostatin protein purification capture step, and the specific resin used is called STREAMLINE™-SP sulfopropyl resin (Pharmacia, Inc.). SP refers to the sulfopropyl functional groups that are attached to the support bead that give the resin its cationic character. It is to be understood that besides STREAMLINE™-SP resin, other resins that act as cation exchangers may be used in the practice of the present invention. Such cation exchangers include but are not limited to carboxymethylcellulose. STREAMLINE™ refers to a relatively new format of chromatography that is designed to capture and separate target protein from a milieu of broth, thus eliminating the need for centrifugation to separate cells from the protein-containing supernatant. This type of chromatography is also known as expanded bed absorption chromatography (EBA). In practice, the broth is typically pumped up into a STREAMLINE™ column containing about 20-30% by volume of settled resin and approximately 70-80% buffer. As the broth enters the column, the bed of resin expends and flows up, thereby accounting for the name EBA. As the bed flows up, protein is bound to the beads, which can only flow up a finite distance, to an equilibrium level. The cells and non-bound protein however, flow up and out of the column to waste. Once all the broth has been pumped onto and traversed the column, the flow direction is reversed (now in the downward direction) and the resin is allowed to pack. What remains is a functional column that can be washed and eluted in the more conventional sense. Endostatin protein is eluted from this column with salt, and is ready for the next chromatographic step.

The next chromatographic step in the process is to apply the sample to a Heparin-SEPHAROSE™ Fastflow agarose bead column (Pharmacia, Inc.). In this column, heparin, a negatively-charged molecule, is covalently attached to a Fastflow SEPHAROSE™ agarose bead support. Heparin columns are relatively expensive and are difficult to sterilize with addition of strong base such as NaOH.

In an alternative embodiment of the present invention, the heparin column may be replaced with a column employing a resin appropriate for hydrophobic interaction chromatography (HIC). The HIC column is less expensive and easier to maintain than the heparin column. The HIC column also offers the benefit of requiring less volume of elution buffers. Using a HIC column, the sample may be loaded at one end of the column and elution buffer may be applied from the other end of the column to elute the desired material from the column, thereby decreasing the volume of required elution buffer. In this manner, a lower volume of sample in buffer is produced and a lower volume of buffer containing sample must be processed through the next step of diafiltration in the procedure. In one embodiment, a phenyl SEPHAROSE™ Fastflow agarose bead column (Pharmacia, Inc.) is employed as the HIC column.

Another advantage of employing the HIC column instead of the fast flow heparin SEPHAROSE™ column is that the HIC column effectively removes various pigments, cytochromes such as cytochrome C, and proteins present in the cells and cellular extracts of the expression system. Pigments are a concern when using some expression systems, such as *Pichia pastora*-based fermentation systems. An advantage of using the HIC column is that when the sample processed through the HIC column is next applied to the SP column, the SP column has a higher loading capacity and performs more efficiently, thereby producing better separations. Another advantage of the HIC column is that it withstands conditions that are too severe for the heparin column. The HIC column is less expensive, may be cleaned with 0.5 M NaOH, and exhibits a longer life than the heparin column. Accordingly, although heparin columns may be used, HIC columns are used in an alternative embodiment of the present invention.

The next chromatographic step consists of two steps that are combined. Two columns are connected and run in tandem. They are, in order, a quaternary amine (O) column, which is an anion exchange column, and an SP-cation exchange column. The Q column is used to remove DNA and endotoxin primarily, and some host cell proteins secondarily. The SP column serves to recapture and concentrate endostatin protein, and to separate a pigment contaminant, cytochrome C, from endostatin protein. Pigments are a concern when using *Pichia pastoris*-based fermentations. Importantly, this SP column, which actually uses similar chemistry as the STREAMLINE™ column, is impacted directly by the above-mentioned addition of a HIC column to the purification process since a HIC column removes most if not all of the cytochrome C pigment upstream of the final SP column. This results in removing the chromatography function (pigment removal) of the final SP column and allowing the final SP column to function more as a re-capture and concentration column. The efficiency and loading capacity of the SP column are increased significantly and larger endostatin protein batches may be purified.

The final step in the purification procedure involved concentration and dialysis using the approach of Ultrafiltration/Diafiltration (UF/DF). In this step, the sample from the preceding step is pushed through a membrane, preferably made from polyethersulfone, with a molecular cutoff chosen to retain endostatin protein or another protein of interest on the membrane. A preferred molecular cutoff for endostatin protein is about 3 kDa. Several liters of formulation buffer are run over the membrane to recover retain endostatin protein, or another protein of interest remaining in the filters. This material recovered from the filters is added to the pool of endostatin protein. In another embodiment of the present invention, parallel flow concentrators employing porous tubes may be used instead of flat membranes for concentration and dialysis.

Buffers for Optimal Solubility, Storage and Lyophilization of Endostatin Protein Solubility of Endostatin Protein During scale up of the endostatin protein purification process described in the present patent application, it was determined that endostatin protein precipitates under certain conditions. Purified protein fermented in shakers precipitated after dialysis in water. Dialysis was improved by addition of 0.1× phosphate buffered saline (PBS, i.e., a 10% solution of PBS), however minor precipitation of the protein was still observed at protein concentrations of at least 0.5 mg/ml. Purified protein solutions of about 2.16 mg/ml in PBS demonstrated minor precipitation after storage at −80° C. Precipitation of the protein was significantly increased when the protein was purified at acidic pH; for example, purified protein in concentrations of 0.1 to 0.2 mg/ml readily precipitated in 10 mM acetate buffer at a pH of 4.0. Purified protein in concentrations of greater than or equal to about 0.4 mg/ml precipitated in 10 mM acetate buffer at a pH of around 5.0, and severe precipitation was observed during diafiltration with this buffer. Therefore, as with most proteins, the solubility of endostatin protein is correlated to buffer pH and ionic strength.

The selection of a buffer formulated to provide optimal solubility conditions for endostatin protein, which do not adversely affect bioactivity and also favor storage, is important for the final dilution of purified endostatin protein. In this step, the material that is eluted from the final SP column is concentrated to a convenient concentration, such as 8 mg/ml, and diafiltered into the proper citrate-phosphate sodium chloride buffer. Previously, a citrate-phosphate buffer that contained no sodium chloride was employed. It was observed that this buffer was subject to rapid precipitation at the diafiltration step. As sodium chloride was removed, the protein began to precipitate, so sodium chloride was added as a component of the final formulation buffer. The final formulation buffer is 17 mM citric acid, 66 mM dibasic sodium phosphate, 59 mM sodium chloride, pH 6.2.

In order to examine solubility of recombinantly-produced endostatin protein, especially endostatin protein produced from *Pichia pastoris*, dialysis studies were performed using commercially available dialysis membranes loaded with protein solution containing endostatin protein. The analysis of purified endostatin protein was conducted using spectrophotometry, particularly near-UV spectrophotometry. Protein concentrations were determined based on extinction coefficient values and absorption ratios were also examined.

The maximum solubility of endostatin protein was determined in different buffering systems. Endostatin protein was added to different buffer systems and concentrated using a centrifugal filter device until minor aggregation was visualized. Soluble protein was scanned and the concentration was determined as described above. A fixed amount of purified endostatin protein was loaded into dialysis membranes and a variety of Tris-HCl buffers in a wide range of concentrations were examined at different temperatures. After filtering with a sterile filter, the soluble protein was scanned and the concentration determined. The ionic strengths and pHs of different buffers such as citrate-phosphate and Tris-HCl were examined.

A range of endostatin protein concentrations diluted in 200 mM citrate-phosphate buffers were frozen in dry ice, maintained at −70° C. and lyophilized. The effects of lyophilization were tested by analyzing the protein concentration before and after lyophilization. A variety of analytical techniques including HPLC, size exclusion chromatography (SEC), cat-ionic HPLC, and reversed phase HPLC were employed to examine the elution properties of endostatin protein. Endostatin protein was analyzed according to the different solubility paradigms. Purity of endostatin protein was examined using non-denaturing sodium dodecyl sulfate (SDS) discontinuous gel electrophoresis and western blots. Monoclonal antibodies against endostatin protein were used to probe the Western blots and densitometric measurements were obtained. These various techniques rendered possible the analysis of the solubility characteristics of recombinantly produced endostatin protein in different buffer systems, at different osmotic strengths of these buffer systems, and at different pH and temperature.

This invention is further illustrated by the following examples, which are not to be construed in any way as imposing limitations upon the scope thereof. These conditions for endostatin protein production and/or purification may be scaled up, for example, by 5, 10, 20 or 100 fold to accommodate the need for large scale endostatin protein production. On the contrary, it is to be clearly understood that resort may be had to various other embodiments, modifications, and equivalents thereof which, after reading the description herein, may suggest themselves to those skilled in the art without departing from the spirit of the present invention.

EXAMPLE 1

Cloning of Human Endostatin Protein Gene Fragment in *Pichia pastoris*

1. EM6688 The gene encoding the 183 amino acids of human endostatin protein was cloned and expressed under the strong inducible AOXI promoter in *P. pastoris*. The expressed protein was targeted for secretion in the broth of *P. pastoris* cultures as a soluble product upon methanol induction.

The sequence encoding endostatin protein was amplified by PCR using Taq DNA polymerase (Stratagene, La Jolla, Calif.), forward primer #306 (5' TCT CTC GAG AAA AGA CAC AGC CAC CGC GAC TTC CA (SEQ ID NO:1)) and reverse primer #295 (5' ATC GTC TAG AGC ATC CAG GCG GTG GCT ACT (SEQ ID NO:2)) containing linkers with XhoI and XbaI restriction sites, respectively, and the plasmid CTB08#5 (Gift from T. Boehm, Children's Hospital, Boston) as template. The PCR product was gel purified using the Gel Extraction Kit (QIAGEN, Inc.), linkers digested with restriction enzymes XhoI and XbaI (Life Technology, Gaithersburg, Md.) and further gel purified before ligation into the XhoI/AvrII site of the vector pPIC9K (Invitrogen, San Diego, Calif.), and transformation into competent DH5 *E. coli* cells (Life Technologies, Gaithersburg, Md.). The clone pPIC9K/HEsv2/14 was selected and the integrity of the DNA sequence was verified. Plasmid DNA from clone pPIC9K/HEsv2/14 was prepared using Qiagen Plasmid Maxi Kit (QIAGEN, Inc.), linearized with Sal I (Life Technology, Gaithersburg, Md.), and transformed into the *P. pastoris* host strain GS 115 (Invitrogen, San Diego, Calif.) by electroporation. Transformants were selected on MD (minimal dextrose) plates followed by selection on yeast extract peptone dextrose (YPD) containing G418. Selected transformants were grown from single colonies on YPD containing G418. Expression was followed upon methanol induction and growth in BMGY/BMMY media, and analyzed on Coomassie stained SDS-PAGE gels and immunoblots using a mouse monoclonal antibody against human endostatin protein (gift from T. Boehm, Children's Hospital, Boston). The endostatin protein production clone EM6688 was selected and its phenotype was identified as His+Mut+ by plating onto minimal media in methanol (MM) and MD plates.

Sequence of Human Endostatin Protein

The following is an example of a functional human endostatin protein of the present invention. This is the endostatin protein amino acid sequence encoded by the gene sequence listed below as SEQ ID NO:3.

Human endostatin protein sequence, 183 aa (SEQ ID NO:3) HSHRDFQPVLHLVALNSPLSGGMRGIR-GADFQCFQQARAV GLAGTFRAFLSSRLQDLYSIVR-RADRAAVPIVNLKDELLFPS WEALFSGSEGPLKP-GARIFSFDGKDVLRHPTWPQKSVWHG SDPNGRRLTESYCETWRTEAPSAT-GQASSLLGGRLLGQSAA SCHHAYIVLCIENSFMTASK The following sequence is a nucleotide sequence (SEQ ID NO:4) for a representative gene encoding for the endostatin protein shown above as (SEQ ID NO:3). Nucleotide sequence encoding for human endostatin protein, 549 bp (SEQ ID NO:4) CACAGCCACCGCGACTTCCAGCCGGT-GCTCCACCTGGTT GCGCTCAACAGCCCCCTGTCAG-GCGGCATGCGGGGCATC CGCGGGGCCGACTTC-CAGTGCTTCCAGCAGGCGCGGGCC GTGGGGCTGGCGGGCACCTTCCGCGCCT-TCCTGTCCTCG CGCCTGCAGGACCTGTACAG-CATCGTGCGCCGTGCCGAC CGCGCAGCCGTGC-CCATCGTCAACCTCAAGGACGAGCTG CTGTTTCCCAGCTGGGAGGCTCTGTTCT-CAGGCTCTGAGG GTCCGCTGAAGCCCGGGGCACG-CATCTTCTCCTTTGACG GCAAGGACGTCCTGAG-GCACCCCACCTGGCCCCAGAAG AGCGTGTGGCATGGCTCGGAC-CCCAACGGGCGCAGGCTG ACCGAGAGCTACTGT-GAGACGTGGCGGACGGAGGCTCC CTCGGC-CACGGGCCAGGCCTCCTCGCTGCTGGGGGCAG GCTCCTGGGGCAGAGTGCCGCGAGCTGC-CATCACGCCTA CATCGTGCTCTGCATTGAGAA-CAGCTTCATGACTGCCTCC AAG As described above, different recombinant endostatin proteins have been isolated from the fermentation broth from clones containing the nucleotide sequence shown in SEQ ID NO:4. These different forms of endostatin protein contain deletions of the C-terminal 1, 2, and 3 amino acids (aa) and are shown below as SEQ ID NOS: 5, 6, and 7.

Human endostatin protein: C terminus minus 1 amino acid, lysine, at position 183 (182 amino acids (SEQ ID NO:5)) HSHRDFQPVLHLVALNSPLSGGMRGIR-GADFQCFQQARAV GLAGTFRAFLSSRLQDLYSIVR-RADRAAVPIVNLKDELLFPS WEALFSGSEGPLKP-GARIFSFDGKDVLRHPTWPQKSVWHG SDPNGRRLTESYCETWRTEAPSAT-GQASSLLGGRLLGQSAA SCHHAYIVLCIENSFMTAS Human endostatin protein: C terminus minus 2 amino acids, lysine and serine at positions 183 and 182, respectively (181 aa (SEQ ID NO:6)) HSHRDFQPVLHLVALNSPLSGGMR-GIRGADFQCFQQARAV GLAGTFRAFLSSRLQDL-YSIVRRADRAAVPIVNLKDELLFPS WEALFSGSEG-PLKPGARIFSFDGKDVLRHPTWPQKSVWHG SDPNGRRLTESYCETWRTEAPSAT-GQASSLLGGRLLGQSAA SCHHAYIVLCIENSFMTA Human endostatin protein: C terminus minus 3 amino acids, lysine, serine, and alanine at positions 183, 182, and 181, respectively (180 aa (SEQ ID NO:7)) HSHRDFQPV-LHLVALNSPLSGGMRGIRGADFQCFQQARAV GLAGTFRAFLSSRLQDLYSIVR-RADRAAVPIVNLKDELLFPS WEALFSGSEGPLKP-GARIFSFDGKDVLRHPTWPQKSVWHG SDPNGRRLT-ESYCETWRTEAPSATGQASSLLGGRLLGQSAA SCHHAYIVLCIENSFMT The species represented as C terminus minus 1 amino acid (SEQ ID NO:5, 182 aa) is the preferred endostatin protein of the present invention that is isolated from the *Pichia pastoris* system wherein the clone has the nucleotide sequence shown in SEQ ID NO: 4. However, it is to be understood that the term "endostatin protein", as defined above and as encompassed within the present invention, includes a variety of forms of endostatin protein, including but not limited to forms that are lengthened or shortened by one or more amino acids, at either or both ends, or at an internal location, of the endostatin protein provided the resulting molecule retains endothelial proliferation inhibiting activity.

In addition to the human endostatin proteins described above in SEQ ID NOS: 5, 6, and 7, another endostatin protein variant occurs (SEQ ID NO: 11), which is the former protein (SEQ ID NO:5) minus the first four amino acids at the N-terminus (N 1-4). Yet another endostatin protein variant occurs (SEQ ID NO: 8), which is the former protein (SEQ ID NO:3) minus the first four amino acids at the N-terminus (N 1-4). These variants of endostatin protein, obtained from *Pichia pastoris* containing the nucleotide sequence shown in SEQ ID NO: 4, demonstrate the variability of human endostatin protein molecules encompassed within the scope of the present invention.

2. hESv3 human endostatin protein was also expressed from clones without the nucleotides encoding for the first 4 (N-terminal) amino acids (N-4) (hESv3) in *P. pastoris* by amplifying the gene fragment encoding human endostatin protein (SEQ ID NO:8, N-4) using the forward and reverse primers #359 5' TCT CTC GAG AAA AGA GAC TTC CAG CCG GTG CTC (SEQ ID NO:9) and #295 5' ATC GTC TAG AGC ATC CAG GCG GTG GCT ACT (SEQ ID NO:2) respectively, using the same strategy as for the gene encoding full length human endostatin protein. The shuttle plasmid used for transforming GS 115 was pPIC9K/hESv3/27. The phenotype of the *P. pastoris* clone expressing recombinant human endostatin protein (N-4) that was selected for study was identified as His+Mut+.

Gene sequence, 537 bp (SEQ ID NO: 10), encoding for human endostatin protein wherein the N-terminal 4 amino acids (1-4) are removed and the C-terminal lysine is present (shown as SEQ ID NO:8).

GACTTCCAGCCGGTGCTCCACCTGGT-
TGCGCTCAACAGC CCCCTGTCAGGCGGCAT-
GCGGGGCATCCGCGGGGCCGAC TTCCAGTGCTTC-
CAGCAGGCGCGGGCCGTGGGGCTGGCG
GGCACCTTCCGCGCCTTCCTGTC-
CTCGCGCCTGCAGGACC TGTACAGCATCGTGCGC-
CGTGCCGACCGCGCAGCCGTGC CCATCGTCAACCT-
CAAGGACGAGCTGCTGTTTCCCAGCT
GGGAGGCTCTGTTCTCAGGCTCT-
GAGGGTCCGCTGAAGC CCGGGGCACGCATCT-
TCTCCTTTGACGGCAAGGACGTCC TGAGGCAC-
CCCACCTGGCCCCAGAAGAGCGTGTGGCATG
GCTCGGACCCCAACGGGCGCAGGCTGAC-
CGAGAGCTACT GTGAGACGTGGCGGACGGAG-
GCTCCCTCGGCCACGGGC CAGGCCTCCTCGCT-
GCTGGGGGGCAGGCTCCTGGGGCAG
AGTGCCGCGAGCTGCCATCACGCCTA-
CATCGTGCTCTGC ATTGAGAACAGCTTCATGACT-
GCCTCCAAG

Alternate human endostatin protein sequence, 179 aa (SEQ ID NO:8) wherein the N-terminal 4 amino acids (1-4) are removed and the C-terminal lysine is present. DFQPV-LHLVALNSPLSGGMRGIRGADFQCFQQARAVGLAG TFRAFLS SRLQDLYSIVRRADRAAVPIVNLKDELL-FPSWEAL FSGSEGPLKPGARIFSFDGKDVLRHPTW-PQKSVWHGSDPNG RRLTESYCETWRTEAPSAT-GQASSLLGGRLLGQSAASCEH AYIVLCIENSFMTASK Alternate human endostatin protein sequence isolated from *Pichia pastoris*, wherein the N-terminal 4 amino acids (1-4) are removed and the C-terminal lysine is absent (178 aa (SEQ ID NO: 11)).

DFQPVLHLVALNSPLSGGMRGIRGAD-
FQCFQQARAVGLAG TFRAFLSSRLQDLYSIVR-
RADRAAVPIVNLKDELLFPSWEAL FSGSEGPLKP-
GARIFSFDGKDVLRHPTWPQKSVWHGSDPNG
RRLTESYCETWRTEAPSATGQASSLLG-
GRLLGQSAASCHH AYIVLCIENSFMTAS 3. hESv2/hASv3 The *Pichia* clone expressing both ANGIOSTATIN® protein and endostatin protein (SEQ ID NO:3) was made with the following strategies. The ANGIOSTATIN® gene together with the *Saccharomyces cerevisiae* alpha factor secretory peptide sequence or the gene (SEQ ID NO:4) encoding for endostatin protein together with the *Saccharomyces cerevisiae* alpha factor secretory peptide sequence were PCR amplified and cloned into the EcoRI site of the pAO815 expression vector separately to construct pAO815/hASv3 and pAO815/hESv2 plasmids. The BamHI-BglII fragment from the pAO815/hESv2plasmid containing the endostatin protein expression cassette was subsequently cloned into the BamHI site of the pAO815/hASv3 plasmid, the resulting plasmid DNA was cut with SalI and transformed into GS 115 and selected on minimal dextrose plates (MD). The transformants selected were grown for single colonies on MD plates. Expression was followed upon methanol induction and growth in BMGY/BMMY media and analysis on Coomassie stained SDS-PAGE gels and immunoblots using either a mouse monoclonal antibody against human endostatin protein or polyclonal antibodies against human ANGIOSTATIN® protein. The hESv2/hASv3 production clone produces both human endostatin protein and human ANGIOSTATIN® protein at the same time.

The techniques used in the experiments described above are more fully described in laboratory manuals such as "Molecular Cloning: A Laboratory Manual" Second Edition by Sambrook et al., Cold Spring Harbor Press, 1989; and "Current Protocols in Molecular Biology". John Wiley and Sons, 1995.

EXAMPLE 2

Fermentation Conditions

The methanol feed rate at the 1500 L scale was reduced in comparison to prior runs at a lower scale of 140 L, due to an increase in the ratio of clipped to unclipped protein. Based on experiments, the initial methanol flow rate was reduced from 12.0 mL/L/hr to 8.0 mL/L/hr. An algorithm in a computer program acts as a command loop to test the status of the fermentation in order to determine if more feeding is required based on available carbon. The DO spike test algorithm was changed because the one minute spike test was not performed according to design. The new algorithm locks in the output value prior to the test and then returns to the value after the test is complete. The initial volume was increased from 800 L to 950 L since the harvest volume was well below optimum due to the decrease in the methanol feed volume.

Some production runs of endostatin protein included the high trace salts fermentation steps. The following are the process changes for the high trace salts fermentation: addition of 0.635M zinc sulfate solution to the main fermentor post sterilization; the PTM4 trace salts were added to the fermentor post sterilization instead of with the methanol feed stream; the methanol ramp rate was reduced to 1.4 mL/kg/hr2—total methanol ramp phase was then 4.8 hours; and the methanol soak phase was increased to 81.2 hours.

The following Table 11 shows two fermentation methods of the present invention that are effective in producing endostatin protein.

TABLE 11

| Parameter | Process 1 | Process 2* |
|---|---|---|
| Temperature | 30° C. | 30° C. |
| Pressure | 0.2 bar | 0.2 bar |
| Agitation | constant | constant |
| Aeration | 0.7 VVM with $O_2$ supplementation based on culture demand | 0.7 VVM with $O_2$ supplementation based on culture demand |
| Initial batch of PTM4 trace salts | 2 mL/L | 3.5 mL/L |
| Zn supplementation (stock solution of 0.635 M Zn sulfate $7H_2O$ | none | 1.7 mL/L |

TABLE 11-continued

| Parameter | Process 1 | Process 2* |
| --- | --- | --- |
| Duration of the glycerol fed-batch phase | 6 hours | 6 hours |
| Glycerol feed addition rate | 15 (mL/L/hr) (16.6 g/kg/hr) | 15 (mL/L/hr) (16.6 g/kg/hr) |
| Methanol feed consumption | 2 mL/L of PTM4 trace salts | none |
| Methanol ramp | 0.5 mL/L/hour per hour | 1.5 mL/L/hour per hour |
| Methanol maximum constant rate | 12 mL/L/hour | 8-12 mL/L/hour |
| Duration of the methanol fed-batch phase | 72 hours | 86 hours |

*Process is currently a preferred process. Process 2 is also called the high salts fermentation process.

EXAMPLE 3

STREAMLINE™ SP Chromatography of Endostatin Protein

The entire process was performed at room temperature. The column dimensions were about 60 cm in diameter by 90 cm in height. Settled bed height was approximately 23 cm which corresponds to about 65 to 70 liters of STREAMLINE™ SP resin (approximate particle size of 200 µm). The expanded bed height was approximately 85±15 cm, and the expanded volume was about 210 liters. The flow rate of this column was approximately 848±40 liters per hour (LPH) which is about 14 liters per minute. This corresponds to about 300 cm/hr which is the flow in liters per minute divided by the column diameter. The column was sanitized with 0.5 M NaOH and held for a minimum of 6 hours. The column was then washed with about 800 liters of buffer (50 mM sodium phosphate, 13 mM citric acid, 10% glycerol, pH 6.3). An alternative equilibration buffer used at this step, although less preferred than buffers containing glycerol, was 50 mM sodium phosphate, 24 mM citric acid, pH 5.1, which was employed until the pH and conductivity of the column were the same as that of the buffer. Buffer was introduced at the bottom of the column and moved upward through the column, at a total flow rate of approximately 848±40 LPH. Overflow from the column was directed to a drain.

The fermentation mixture was then diluted about 5 to 7-fold with water at a temperature of 10±5° C., to attain a target conductivity of approximately 6.5±1.5 milliSiemens (mS)/cm and a pressure of 3±1 psig. The fermentation mixture was next loaded onto the bottom of the column, in an upward direction, at a conductivity of approximately 6.5±1.5 mS/cm. The total flow rate was about 848±40 LPH (3.7±0.2 gallons per minute; 300 cm/hour) and the maximum column pressure was about 22 psig. Overflow from the column was directed to a drain.

Endostatin protein was then eluted from the column by introducing elution buffer (17 mM citric acid, 66 mM sodium phosphate, 250 mM NaCl, pH 6.3) at the top of the column and flowing the buffer in the downward direction at a rate of 848±40 LPH and a maximum pressure of 22 psig. A minimum volume of about 800 liters may be processed.

This STREAMLINE™ column was regenerated and stored by using the following six step procedure.

1. First, about 450±50 liters of 2 M NaCl (regeneration buffer) was introduced at the bottom of the column and flowed in the upward direction at a rate of 848±40 LPH and a maximum column pressure of 22 psig.

2. Next, about 300±20 liters of 6 M urea, a second regeneration buffer, was recirculated through the column, from the bottom of the column to the top, at a maximum column pressure of about 22 psig.

3. After recirculating about 200 liters of the urea, the flow direction then moved down through the column for at least 60 minutes.

4. Next, the column was flushed in the downward direction with water until the UV absorbance was less than 0.05 AU at 280 nm.

5. The column was then sanitized with about 550±50 liters of 0.5 M NaOH flowing in the upward direction for a period between about 60 minutes and 180 minutes.

6. The column was then stored in 0.1 M NaOH at a conductivity of about 23±5 mS/cm by running about 450±50 liters through the column in the downward direction.

EXAMPLE 4

Heparin SEPHAROSE™ FastFlow Chromatography of Endostatin Protein

The column dimensions were about 45 cm in diameter by 25 cm in height and the bed volume was about 40 liters. The maximum pressure applied to the column was about 2 bars. The column was sanitized in 0.1 M NaOH buffer before application of sample. About 150 liters of the buffer flowed downward through the column at 480 liters per minute (LPM). The column and associated chromatography apparatus was held in 0.1 M NaOH for a minimum of about 18 hours and a maximum of approximately 48 hours. Next, the NaOH buffer was washed out with about 200 liters of water for injection at a flow rate of 480 LPH until an end conductivity of less than about 1.0 mS/cm was attained. Following the washout of NaOH with water, about 200 liters of an equilibration buffer (20 mM Tris, 50 mM NaCl, pH 7.6) was applied in a downward direction through the column at a flow rate of about 480 LPH. The material eluted from the STREAMLINE™ chromatography step was then diluted with WFI to 3 times its original volume in preparation for loading. Material was loaded and run through the column in a downward direction at a rate of about 480 LPH. Next the heparin column was washed in two steps. First, the column was washed with about 150 liters of wash buffer (20 mM Tris, 50 mM NaCl, pH 7.6) in the downward direction at about 480 LPH. Next, about 200 liters of a second wash buffer (a mixture of 80% 20 mM Tris, 50 mM NaCl, pH 7.6 and 20% 20 mM Tris, 500 mM NaCl, pH 7.6) was run down through the column at about 480 LPH. Product was then eluted with about 100 liters of elution buffer (a mixture of 30% 20 mM Tris, 50 mM NaCl, pH 7.6 and 70% 20 mM Tris, 500 mM NaCl, pH 7.6) for about 8 hours at room temperature. Collection began when the UV absorbance rose to about 5% above the baseline. Collection ended when the UV absorbance fell below 5% of baseline. The elution volume was about 1 to 2 column volumes.

The heparin column was regenerated by applying about 120 liters of regeneration buffer (2 M NaCl) in the upward direction at a flow rate of 480 LPH. Next the heparin column was sanitized by applying about 150 liters of the 0.1 M NaOH buffer in the upward direction through the column at approximately 480 liters per minute (LPM). The column and associated chromatography apparatus were held in 0.1 M NaOH for a minimum of about 18 hours and a maximum of approximately 48 hours. About 120 liters of storage buffer (20% ethanol in 50 mM Tris, pH 8.0) was run through the column in a downward direction. The heparin column was stored in this storage buffer.

EXAMPLE 5

Q/SP SEPHAROSE™ Fast Flow Chromatography of Endostatin Protein

The Q and SP SEPHAROSE™ FF columns were operated in tandem since the Q is a negative capture column and the SP a positive capture column. The Q-SEPHAROSE™ FF column was about 30 cm diameter and 13 cm in height with a bed volume of about 10 liters. The SP-SEPHAROSE™ FF column was about 30 cm diameter and 20 cm height with a bed volume of about 20 liters. Pressures in the columns were maintained below 3.5 bar. Both columns were sanitized with about 120 liters of 0.5 M NaOH buffer at a flow rate of about 212 LPH and held in 0.5 M NaOH buffer for at least 1 hour. Next the columns were flushed with water for injection at 212 LPH until the conductivity of the eluate was less than about 1.0 mS/cm.

The columns were charged with about 90 liters of 2 M NaCl at a flow rate of about 212 LPH. Next, about 100 liters of equilibration buffer (20 mM Tris, 50 mM NaCl, pH 7.6) was run through the columns at a flow rate of 212 LPH. Equilibration was complete when the eluate pH was ±0.5 units of the equilibration buffer and eluate conductivity was ±3 mS/cm of the equilibration buffer.

For sample loading on the Q and SP columns, the eluate from the heparin SEPHAROSE™ FF step was diluted, in line with about 5 volumes of water for injection, at a flow rate of 212 LPH. Skid mixing refers to the pumping system which delivers buffers to the columns. In the present invention, skid mixing may be done as follows: 83% WFI valve and 17% elution valve.

The total volume of load was about 6 times the volume of the heparin column elution. Both columns were then washed in about 100 liters of wash buffer (20 mM Tris, 50 mM NaCl, pH 7.6) at a flow rate of 212 LPH. The Q column was then removed from the process. Next, the SP-SEPHAROSE™ FF column was washed with 100 liters of wash buffer at a flow rate of 212 LPH. The wash buffer was a mixture of 80% 20 mM Tris, 50 mM NaCl, pH 7.6, and 20% 66 mM sodium phosphate, 17 mM citric acid, 250 mM NaCl, pH 6.3.

Endostatin protein was eluted from the SP column with a buffer consisting of 66 mM sodium phosphate, 17 mM citric acid, 250 mM NaCl, pH 6.3. Eluate was collected when the UV absorbance rose to more than 5% of the baseline. Elution ended when the UV absorbance returned to 5% or lower of baseline. The elution volume was about 1 to 2 column volumes, i.e., the column volume of a SP SEPHAROSE™ column, at an endostatin protein concentration of about 1.5 mg/ml.

The Q-SEPHAROSE™ FF column was regenerated with 30 liters of 2 M NaCl at 212 LPH. The SP-SEPHAROSE™ FF column was regenerated with 60 liters of 2 M NaCl at 212 LPH. Both columns were sanitized with about 120 liters of 0.5 M NaOH at a flow rate of 212 LPH for between approximately 60 and 120 minutes, and held for at least one hour. For storage of both columns, about 150 liters of 0.1 M NaOH was introduced into the columns at a flow rate of about 212 LPH.

EXAMPLE 6

Ultrafiltration/Diafiltration (UF/DF)

The final step in the procedure involved concentration and dialysis using the approach of Ultrafiltration/Diafiltration (UF/DF). The equipment for UF/DF included a membrane of about 25 sq. ft., made of polyethersulfone with a 3 kDa cutoff (Item # 401-01938, Pall Filtron Cassette, Pall Filtron, Northborough, Mass.). A peristaltic pump, such as a Watson Marlow #6035, or an equivalent with Masterflex tubing #06485-18 was employed.

Before beginning UF/DF of the sample, the membrane was sanitized with 50 liters of 0.5N NaOH for at least 60 minutes and no more than 120 minutes. Next, the membrane was flushed with about with 150 liters of water for injection. The retentate and permeate were measured to ensure that the conductivity was equal to water. The system integrity was checked after each use by measuring the normalized water permeability. After each membrane use for UF/DF, a new membrane was employed if the normalized water permeability was not more than 75% of the original new membrane. The integrity of the filter is checked by applying pressure to the filter and using a device known to one of skill in the art to test integrity of the filter.

Next, the membrane system was equilibrated with 40 liters of formulation buffer consisting of 17 mM citric acid, 66 mM sodium phosphate, 59 mM NaCl, pH 6.2. The conductivity of the permeate and retentate streams was ±1 mS/cm and pH was ±0.1 pH units of the formulation buffer.

The following describes the ultrafiltration parameters employed. The target concentration of endostatin protein was about 8 g/L, and the concentration time was about 8 hours at 18-20° C. The retentate rate was approximately 10±5 LPM. Inlet pressure was about 20-25 psig and the retentate pressure was approximately 13-20 psig. The TMP value (wherein TMP={(Inlet pressure+outlet Pressure/2)−Permeate Pressure}) was about 16-21 psig. The permeate pressure was equal to 0 with a fully opened valve.

The following describes the diafiltration parameters that were used. First, the volume of formulation buffer needed for a 7 fold diafiltration was calculated. The retentate rate was about 10±5 LPM. Inlet pressure was approximately 20 to 25 psig and the retentate pressure was about 13 to 20 psig. The TMP value was about 16 to 21 psig, where TMP is defined as described above. Diafiltration with formulation buffer was continued until the permeate volume was equal to the volume calculated above (the 7 fold diafiltration volume). Next, the permeate valve was closed and retentate valves were opened. The diafiltration buffer was recirculated at 0-5 psig for 5-10 minutes. The conductivities of the UF/DF streams were compared to that of the formulation buffer. The permeate conductivity was about 16.0±5.0 mS/cm, and the permeate pH was about 6.2±0.2 pH units.

Next the UF/DF filters were rinsed twice with about 1.5 liters of formulation buffer to recover material remaining in the filters. This material recovered from the filters was added to the pool of ENDOSTATIN. The pump speed was set to approximately 20% of maximum and formulation buffer was recirculated with no back pressure for about 10 to 15 minutes. The eluate in the flushes was monitored by UV absorbance. If UV absorbance at 280 nm was less than 0.10, the operation was stopped.

The performance of the UF/DF membranes was closely monitored. The normalized water permeability must be 75% of that value obtained with new membranes. Currently, new UF/DF membranes were used for each 2000 liter fermentation run.

The UF/DF system was then sanitized with 0.5M NaOH which was recirculated for no less than 60 and no more than 120 minutes. Next the system was flushed with water for injection. The UF/DF system was stored in 0.1M NaOH.

EXAMPLE 7

Buffer Systems for Optimal Solubility of Recombinant Endostatin Protein

As mentioned above, the formulation buffer used in the UF/DF step was 17 mM citric acid, 66 mM sodium phosphate, 59 mM NaCl, pH 6.2. This example presents results from testing a variety of different buffer systems to determine the optimal buffer for endostatin protein solubility. Such information is needed for choosing the buffer systems for use in the various steps in the purification process, for use in storage at various temperatures, and for lyophilization of endostatin protein.

Dialysis

All dialyses were performed at 4° C. for 24 hours with two buffer changes unless otherwise indicated. Protein solution was loaded into a 7.5 mm×5 cm Spectra/Por (3.5 kD cutoff) dialysis membrane. Air was sealed in the bag using clamps, which allows only a limited amount of buffer to enter and dilute the protein.

Analysis of Purified Endostatin Protein Using Near—UV Spectrophotometry

A Perkin Elmer Lambda 2 UV/Vis spectrometer was used to scan from 350 nm to 210 nm. The protein concentration was calculated based on extinction coefficient value of 1.34 at 280 nm for 1.0 mg/ml endostatin protein (Gill and von Hippel, 1989). The absorption ratio of 280 nm vs. 260 nm was also determined.

Maximum Solubility of Endostatin Protein in Different Buffering Systems

Purified endostatin protein in 10 mM Tris-HCl or PBS was concentrated using a Millipore centrifugal filter device (15 ml, Biomax, 5k NMWL membrane) until minor aggregation was visualized. After dialysis, the protein was filtered with a 0.2 µm sterile filter. The soluble protein was scanned and its concentration was measured as described above.

Effects of Temperature and Ionic Strength on Solubility of Purified Human Endostatin Protein One ml of purified endostatin protein, with a concentration of 8 mg/ml in PBS, was loaded into a 7.5 mm×5 cm Spectra/Por (3.5 kD cutoff) dialysis membrane. Twelve tubes were dialyzed against pH 7.4 Tris-HCl buffer at concentrations of 10, 25, 50, 100, 150 and 250 mM, at both 4° C. and 22° C. After filtering with a 0.2 µm sterile filter, the soluble protein was scanned and its concentration was determined.

Effects of pH and Ionic Strength on Solubility of Purified Human Endostatin Protein Ionic strengths of 10 mM and 250 mM were chosen based on the study of the effects of temperature and ionic strength on solubility of purified human endostatin protein. About 1 ml of purified endostatin protein, with a concentration of 2 mg/ml in PBS, was loaded into a 7.5 mm×5 cm Spectra/Por (3.5 kD cutoff) dialysis membrane. Twenty-five tubes were dialyzed at 4° C. against different buffers from pH 4.2 to 9.0. The buffers included 10 mM or 250 mM citrate-phosphate pH 4.2, 4.6, 5.0, 5.4, 5.8, 6.2 and 6.6; and 10 mM or 250 mM Tris-HCl pH 7.0, 7.4, 7.8, 8.2, 8,6 and 9.0. After filtering with a 0.2 µm sterile filter the soluble protein was scanned and its concentration was determined.

Effect of Lyophilization on Solubility of Endostatin Protein

Endostatin protein (44 mg/ml) was serially diluted with 200 mM citrate-phosphate buffer to several final concentrations including 0.73, 1.45, 2.92, 5.84, 11.7 and 17.5 mg/ml. The vials were quick-frozen in dry ice, kept at −70° C. for two days and then lyophilized. The lyophilized protein was dissolved in 200 mM citrate-phosphate buffer, pH 6.2 and filtered with a 0.2 µm filter. The soluble protein concentration was determined before and after lyophilization.

High-Performance Liquid Chromatography (HPLC) Assays

All HPLC work was carried out using a Waters 600 controller, 996 Photodiode Array Detector, and 600 pumps. Data were analyzed using Millennium software.

SEC High-Performance Liquid Chromatography

A Protein Pak 125 column was equilibrated with 200 mM citrate-phosphate buffer, pH 6.2. Five µl of 17 mg/ml endostatin protein were loaded onto the column and the protein was eluted at a flow rate of 1 ml/min and monitored at 280 nm. Total run time was 40 minutes. For samples before and after lyophilization, 5 µl of 1 mg/ml endostatin protein were loaded onto an analytical Biosep-s3000 (Phenomenex) column and the protein was eluted at a flow rate of 0.25 ml/min. Total run time was 40 minutes.

Cationic High-Performance Liquid Chromatography

Briefly, endostatin protein was diluted with 10 mM acetate buffer, pH 4.0, to reduce the conductivity to 5 mS or below. Acetate buffer (10 mM, pH 4.0), was used as mobile phase A, and 2M NaCl in the same buffer was used as mobile phase B. The sample was loaded onto the Hs strong cationic column, which was equilibrated with mobile phase A. Extraneous protein was eluted with 30% of mobile phase B equivalent to 600 mM NaCl in 10 mM acetate buffer, pH 4.0. endostatin protein was specifically eluted with 2 M NaCl in 10 mM acetate buffer. The peak area for endostatin protein was integrated by the software.

Reverse Phase High-Performance Liquid Chromatography

Deionized water containing 0.1% TFA was used as mobile phase A and 60% acetonitrile in water (v/v) containing 0.1% TFA was used as mobile phase B. After loading, unbound material was removed with 100% mobile phase A for 5 minutes with a flow rate of 0.2 ml/min. The gradient was 0% B to 100% B in 30 minutes. The $C_4$ column (Vydax) was cleaned using 100% B for 5 minutes and equilibrated with 100% A for 5 minutes. Absorption of protein was monitored at 280 nm and integrated by the chromatography software.

Protein Purity Assays by SDS-PAGE and Western Blot

Non-denaturing SDS discontinuous gel electrophoresis (Laemmli et. al., 1977) with 4-20% gradient pre-cast slab gels and Western blot were used to determine the purity and covalent aggregate state of endostatin protein before and after treatments. A monoclonal antibody against human endostatin protein (a gift from Dr. Thomas Boehm, Children's Hospital, Harvard Medical School, Boston, U.S.A.) used to probe these Western blots. It was raised in mice using synthetic peptide immunogen COOH-CKDELLFPSWEALFSGSEGPLKP-GAR-NH$_2$ (SEQ ID NO: 12) from human collagen-18. It does not recognize human or mouse collagen 15, or mouse ENDOSTATIN.

Results indicated that endostatin protein displayed different solubilities at 22° C. and 4° C. While no precipitation was observed for the protein examined at 22° C. in the Tris-HCl buffer at pH 7.4 at concentrations from 10 mM to 250 mM, the behavior of endostatin protein was quite different at 4° C. Severe precipitation was observed at 4° C. using 100 mM Tris-HCl, slightly less at a 150 mM Tris-HCl and minor precipitation was observed at 50 mM Tris-HCl. Dialysis at 250 mM Tris-HCl pH 7.4 resulted in the most soluble protein, whereas dialysis at 10 mM Tris-HCl was second in terms of protein solubility while dialysis at 100 mM Tris-HC 1 was least favorable to endostatin protein solubility. While not wanting to be bound by the following explanation these results may be consistent with a salting out and salting in phenomenon.

The study of the effects of pH and ionic strength on solubility of purified endostatin protein showed that when the ionic strength of the buffer was 250 mM, solubility was only slightly affected by pH. However, at 10 mM citrate-phosphate buffer, the protein had a maximum solubility at pH 6.2, but displayed poor solubility in this buffer at pH values below 5.0 and above 7.0. This result was unexpected since the experimental pI of endostatin protein was determined to be 9.5.

Endostatin protein solubility appears to be optimal when two physical factors, namely pH of 6.2 and high ionic strength, are combined. The solubility of endostatin protein is about 102.6 mg/ml at 200 mM citrate-phosphate buffer and 78.68 mg/ml at 150 mM citrate-phosphate buffer. Single freeze thaw steps did not affect endostatin protein solubility at 200 mM citrate-phosphate buffer, pH 6.2. Aggregates of endostatin protein were not detected by HPLC-SEC chromatography. Covalent aggregation was also not observed when examined with non-reducing sodium dodecyl sulfate/polyacrylamide gel electrophoresis (SDS/PAGE) and Western blots for samples of concentrations of 102 mg/ml before and after freeze thaw. In contrast to the results obtained in citrate-phosphate buffers, maximum solubility of endostatin protein was 8.0 mg/ml in PBS at pH 7.4 and 7.9 mg/ml in 10 mM Tris-HCl buffers at pH 7.4. However, the solubility of endostatin protein in these buffers was only about 2 mg/ml after a single freeze thaw step. The solubility of endostatin protein was apparently much higher in citrate-phosphate buffer than in either PBS or Tris-HCl systems.

Lyophilization, Solubility and Bioactivity of Endostatin protein

Following lyophilization, solubilization, and filtration, only about 16.5% of endostatin protein was lost. In addition, solubility of endostatin protein was not altered by lyophilization, since analysis with HPLC-SEC chromatography on samples with a concentration of 17.5 mg/ml, both before and after lyophilization, revealed no aggregate formation. This result was in accordance with the results from non-reducing SDS-PAGE Coomassie staining and Western blots. These results indicated no detectable dimers, tetramers or polymers. Further examination of the 16.5% loss of endostatin protein using reverse phase HPLC and cationic HPLC chromatography showed that the protein was lost during filtration since there were no differences in the amount of protein in the samples.

Analysis of the biological activity of purified endostatin protein stored in 200 mM citrate-phosphate buffer at pH 6.2 in comparison to 10 mM Tris-HCl buffer at pH 7.4 showed no differences when measured in the murine B16-BL6 metastatic tumor model. Accordingly, the superior solubility obtained with citrate-phosphate buffer did not influence the biological activity of endostatin protein.

The results of these studies facilitated improvements in the endostatin protein purification scheme. Use of citrate-phosphate buffer, pH 6.2 in the initial dilution of culture medium obtained from the *Pichia pastoris* system significantly increased endostatin protein recovery after downstream processing since endostatin protein washed into the solution from the surface of the cells. In addition, the citrate-phosphate buffer enhanced the binding capacity of endostatin protein to the cationic exchanger, also known as the SP SEPHAROSE™ fast flow. Further benefit was obtained by citrate-phosphate buffer at pH 6.2 improving resolution of SEPHAROSE™ fast flow chromatography. These improvements in recovery of endostatin protein due to enhanced solubility during large scale purifications, such as using the methods of the present invention, facilitate higher yields of endostatin protein through the purification procedure. This process also enhances the solubility of endostatin protein recovered from the purification procedure so that it may be stored under more favorable conditions, and lyophilized without any loss of biological activity or formation of aggregates. These studies also facilitated the production of endostatin protein at a concentration of 102 mg/ml in the 200 mM citrate-phosphate buffer at pH 6.2. Finally, lyophilization in this citrate-phosphate buffer does not affect solubility. These results provide favorable solubility conditions for endostatin protein in different buffering systems and indicate that citrate-phosphate buffer is a preferred buffer for storage and lyophilization of endostatin protein which retains biological activity.

EXAMPLE 8

Process Description for Formulation I of Recombinant Human (rh)Endostatin

Initial Processing of Bulk Protein

A method for the large scale processing of endostatin bulk protein was developed. The starting materials were 1 liter bottles of frozen bulk protein which were thawed overnight in a cold room at 2 to 8° C. This bulk solution was in citrate phosphate saline buffer (17 mM citric acid, 66 mM sodium phosphate, 59 mM sodium chloride). The citrate enhances the solubility of rhendostatin during the Ultrafiltrate (UF) concentration step of the quaternary-amine column and the SP-cation exchange column (Q/SP) eluate up to 10 mg/mL. But, subsequent removal of the citrate was desirable because high local concentrations of citrate may act as an anticoagulant and chelator, and adversely affect subcutaneous injection of the Phase II clinical trial formulations. In order to increase recovery, during the 7× Diafitration step, a ten fold lower amount of sulfated oligo/polysaccharides (0.4 mM), preferably sucrose octasulfate (SOS), was used. This 0.4 mM SOS concentration was adequate to maintain rhEndostatin in solution to greater than 20 mg/mL. A PBS (10 mM phosphate, 115 mM NaCl, ph 7.4)+0.4 mM SOS buffer was prepared. The buffer preferably should be filtered through 0.22 μm sterilizing filter prior to use.

7× Dialfitration (DF) for Replacement of rhEndostatin Buffer

Diafiltration utilizing the PBS+0.4 mM SOS buffer was conducted as described in Example 6 with methods scaled up to 16 liter volumes. The ultrafiltration membrane used was a 2×5 sq ft 3 kD cutoff Regenerated Cellulose Membrane Cassette, Cat. No. CS003C 10 (Pall Filtron), with screen channel. However, other equivalents such as those used in DF/UF of rhEndostatin GMP production may be used. The feed pressure was approximately 40 psi, retentate pressure was approximately 30 psi, retentate flow rate was approximately 1 LPM, and the permeate flow rate was approximately 150 mL/min. Then, 3.6 mM SOS was added to the diafiltered bulk protein as a 0.22 μm filtered 10× concentrate. The approximately 4 mM SOS was required to achieve the target rhEndostatin concentration of 130 mg/mL.

Ultrafiltration (UF) to 40 mg/mL

Ultrafiltration was conducted as described in Example 6 with methods scaled up to 16 liter volumes. Membranes similar to those used for DF may also be used for UF. The starting feed pressure was 41 psi, and the starting retete pressure was 33 psi, and the filtrate flow rate was 134 mL/min. Towards the end of the run, usually 40 minutes, the Feeding Pressure was 46 psi and the retete pressure was 38 psi, with the filtrate flow rate at 114 mL/min. Sterile filtration was then done with a Millipore PVDF 0.22 μm sterilizing filter or an equivalent. The solution was then filled into 3 cc tubing vials, such as West Type I, with 1 mL aliquots per vial.

Lyophilization

Lyophilization required a 48 hour cycle. The filled vials with stoppers at the lyophilization position were loaded onto pre-chilled shelves at low temperatures, preferably less than −40° C. for ease of reconstitution to total clarity. The vials were first frozen for 10 hours, then primary drying was done in three successive steps, at −30° C. for 5 hours, −20° C. for 5 hours and then −10° C. for 10 hours, with chamber pressure set at 100 psi (via nitrogen bleed). A secondary drying, at lowest achievable vacuum, was done in two successive steps at 0° C. for 10 hours and 15° C. for 8 hours. Those skilled in the art should know that the duration of each step was determined by set points for the product temperature. Before proceeding from one step to the next, the product temperature should approximate the shelf temperature within limits pre-established for the lyophilizer.

Stopper and Crimp Seal

Stoppers used can be 13 mm West 4416/50 gray lyophilization stoppers. The vials are stoppered in vacuum or with partial nitrogen overlay.

EXAMPLE 9

Process Description for Formulation II—rhEndostatin/Zinc Chloride (2 Vial System)

Vial 1-rhEndostatin—Initial Processing of Purified Endostatin

The starting materials were 1 liter bottles of frozen bulk protein which were thawed overnight in a cold room at 2 to 8° C. This bulk solution was in citrate phosphate saline buffer (17 mM citric acid, 66 mM sodium phosphate, 59 mM sodium chloride). The citrate enhances the solubility of rhEndostatin during the Ultrafiltrate (UF) concentration step of the quaternary-amine column and the SP-cation exchange column (Q/SP) eluate up to 10 mg/mL. However, subsequent removal of the citrate was desirable because the citrate will chelate zinc, and prevent the zinc from complexing with rhendostatin to form the desired suspension of the Phase II clinical trial formulations. Furthermore, citrate may act as an anticoagulent and chelator, and adversely affect subcutaneous injection of the suspension. The 0.01% Tween 80 solution in Water For Injection (WFI) was added to achieve concentrations of rhendostatin to 40 mg/mL. The Tween 80 was added as a 100× concentrate in ⅖ PBS (40% solution of 10 mM phosphate, 115 mM NaCl, pH 7.4). The ⅖ PBS allows for a 2.5 fold concentration increase during reconstitution with 40% fill volume.

7× Diafitration (DF) for Replacement of rhEndostatin Buffer

Diafiltration was conducted as described in Example 6 with methods scaled up to 16 liter volumes. The ultrafiltration membrane used was a 2×5 sq ft 3 kD cutoff Regenerated Cellulose Membrane Cassette, Cat. No. CS003C10 (Pall Filtron), with screen channel. However, other equivalents such as those used in DF/UF of rhEndostatin GMP production may be used. The feed pressure was approximately 40 psi, retentate pressure was approximately 30 psi, retentate flow rate was approximately 1 LPM, and the permeate flow rate was approximately 150 mL/min.

Ultrafiltration (UP) to 40 mg/mL

Ultrafiltration was conducted as described in Example 6 with methods scaled up to 16 liter volumes. Membranes similar to those used for DF may also be used for UF. The starting feed pressure was 41 psi, and the starting retete pressure was 33 psi, and the filtrate flow rate was 134 mL/min. Towards the end of the run, usually 40 minutes, the feeding pressure was 46 psi and the retente pressure was 38 psi, with the filtrate flow rate at 114 mL/min. Sterile filtration was then done with a Millipore PVDF 0.22 μm sterilizing filter or an equivalent. The solution was then filled into 3 cc tubing vials, such as West Type I, with 2.5 mL aliquots per vial.

Lyophilization

Lyophilization required a 48 hour cycle. The filled vials with stoppers at the lyophilization position were loaded onto pre-chilled shelves at low temperatures, preferably less than −40° C. for ease of reconstitution to total clarity. The vials were first frozen for 10 hours, then primary drying was done in three successive steps, at −30° C. for 5 hours, −20° C. for 5 hours and then −10° C. for 10 hours, with chamber pressure set at 100 psi (via nitrogen bleed). A secondary drying, at lowest achievable vacuum, was done in two successive steps at 0° C. for 10 hours and 15° C. for 8 hours. Those skilled in the art should know that the duration of each step was determined by set points for the product temperature. Before proceeding from one step to the next, the product temperature should approximate the shelf temperature within limits pre-established for the lyophilizer.

Stopper and Crimp Seal

Stoppers used can be 13 mm West 4416/50 gray lyophilization stoppers. The vials were stoppered in vacuum or with partial nitrogen overlay.

Vial 2—Zinc Chloride Solution for Reconstitution Zinc chloride solid was dissolved in WFI to obtain a 20 mM solution. Sterile filtration was then done with a Millipore PVDF 0.22 μm sterilizing filter or equivalent. The solution was then filled into 3 cc tubing vials, such as West Type I, with 1.5 mL aliquots per vial.

Stopper and Crimp Seal

Stoppers used can be 13 mm West 4416/50 gray serum stoppers or its equivalent. The vials were stoppered with nitrogen overlay.

Reconstitution of Biologically Active Endostatin

The contents of Vial 1 were mixed with the contents of Vial 2 and resulted in reconstitution of biologically active Endostatin. The processing above resulted in 100% recovery of Endostatin suitable for use in human clinical studies.

EXAMPLE 10

Alternate Harvest Strategy

In a modified process for separating Endostatin from the fermentation broth, expanded bed chromatography described earlier in the application is replaced with a sludge discharge centrifuge followed by depth filtration. An inline dilution of the harvest broth is included with a target conductivity of <7 mS. The process stream is delivered to the centrifuge at a rate of 60 L/min. The clarified centrate is filtered through a cellulose based depth media followed by pleated filter membranes.

EXAMPLE 11

Alternate Means for Large Scale Purification

Capture: The initial purification of the clarified Endostatin broth is chromatography on a SP-SEPHAROSE™ Fast Flow resin that is operated in a bind and elute mode. The fermentation broth has been clarified using centrifugation and an in-line dilution is performed to obtain a final conductivity of 5-7 mS/cm. The entire contents of the 10 KL fementor are processed on a single cycle on the SP-SEPHAROSE™ Fast Flow column.

Purification: TOYOPEARL™ Phenyl 650M hydrophobic interaction resin is used to selectively bind Endostatin in a hydrophobic interaction type of mechanism. This step is performed at ambient temperature. A gradient system consisting of 3CV is carried out. The column is equilibrated with 66 mM Sodium Phosphate, 17 mM Citric Acid, 2.5M NaCl, pH 6.2 until the pH and conductivity are that of the equilibration buffer. The elution from the STREAMLINE™ SP Chromatography of Endostatin is diluted inline (1×) with 4.5M NaCl and loaded onto the column. The column is first washed with 66 mM Sodium Phosphate, 17 mM Citric Acid, 2.5M NaCl, pH 6.2. The Endostatin is eluted from the column with 20 mM Tris, 50 mM NaCl, pH 7.6. The elute is collected when the UV rises to 0.2 AU and is stopped when the UV returns to 0.2 AU. The elution volume is approximately 1-2 CV's.

Q/SP SEPHAROSE™ FF Chromatography: After the hydrophobic interaction (HIC) step the eluate is 0.2 urn filtered into sterilized single use bags. The material is refrigerated at 2 to 8 degrees C. The purification of the elution from the TOYOPEARL™ Phenyl 650M hydrophobic interaction resin Chromatography is performed in the same manner as before with the exception of a change in the elution buffer. The elution buffer does not contain citrate. The Endostatin is eluted from the SP column with 75% 50 mM Sodium Phosphate, 250 mM Sodium Chloride, pH 7.6 and 25% 20 mM Tris, 50 mM NaCl, pH 7.6. The elute is collected when the UV rises to 0.2 AU and is stopped when the UV returns too less than 0.2 AU. The elution volume is approximately 1-2 CV's of SP SEPHAROSE™ Column.

UF/DF: The concentration/diafiltration of Endostatin is performed in the same manner as before except for the following changes: introduction of 5 Kd Polysulfone membranes, and introduction of a bolus addition of citrate buffer (66 mM Na2PO4, 17 mM Citric Acid, 59 mM NaCl, pH6.2) prior to the start of the concentration/diafiltration.

Formulation: This step of the process remains unchanged. The formulated pool is then aseptically filtered through a 0.21 μm filter. The filtered Endostatin is bulk filled into sterile bottles and then stored at −70° C.

It should be understood, of course, that the foregoing relates only to preferred embodiments of the present invention and that numerous modifications or alterations may be made therein without departing from the spirit and the scope of the invention as set forth in the appended claims.

The invention claimed is:

1. A method of purifying endostatin protein comprising:
   (a) applying a sample comprising endostatin to a first cation exchange column, wherein the first cation exchange column is an expanded bed absorption column, and eluting a first eluate comprising the endostatin from the first cation exchange column using an elution buffer consisting essentially of 17 mM citric acid, 66 mM sodium phosphate, 250 mM NaCl, pH 6.3;
   (b) applying the first eluate comprising the endostatin to a heparin-sepharose column or to a column comprising a resin that selectively binds endostatin via a hydrophobic interaction mechanism and eluting a second eluate comprising the endostatin using an elution buffer consisting essentially of a mixture of 30% 20 mM Tris, 50 mM NaCl, pH 7.6 and 70% 20 mM Tris, 500 mM NaCl, pH 7.6;
   (c) applying the second eluate comprising the endostatin to an anion exchange column and collecting the flow-through comprising the endostatin;
   (d) applying the flow-through comprising the endostatin to a second cation exchange column and eluting a third eluate comprising the endostatin from the second cation exchange column using an elution buffer consisting essentially of 66 mM sodium phosphate 17 mM citric acid, 250 mM NaCl, pH 6.3; and
   (e) concentrating the endostatin.

2. The method of claim 1, wherein the resin that selectively binds endostatin via a hydrophobic interaction mechanism is phenyl sepharose resin.

3. The method of claim 1, wherein the anion exchange column is an amine column.

4. The method of claim 1, wherein first cation exchange column contains sulfopropyl resin or carboxymethylcellulose.

5. The method of claim 1, wherein concentrating the endostatin further comprises pushing the sample through a membrane containing a molecular weight cutoff selected for endostatin and eluting endostatin from the membrane with buffer.

6. The method of claim 5, further comprising lyophilizing the eluted endostatin.

7. The method of claim 5, wherein the membrane is made from polyethersulfone.

8. The method of claim 1, wherein concentrating the endostatin further comprises use of parallel flow concentrators.

9. The method of claim 5, wherein the buffer comprises a citrate-phosphate buffer.

10. The method of claim 9, further comprising removal of citrate by exchanging with phosphate buffered saline and sucrose octasulfate (SOS).

11. The method of claim 10, further comprising lyophilizing endostatin.

12. The method of claim 11, further comprising reconstituting the lyophilized endostatin with a solution.

13. The method of claim 12, wherein the solution is an aqueous zinc chloride solution.

* * * * *